(12) United States Patent
Bowser

(10) Patent No.: US 11,576,825 B2
(45) Date of Patent: Feb. 14, 2023

(54) APPARATUS AND METHOD FOR APPLICATION OF ABSORBENT ARTICLE

(71) Applicant: Medline Industries, Inc., Mundelein, IL (US)

(72) Inventor: William Bowser, Mundelein, IL (US)

(73) Assignee: Medline Industries, LP, Northfield, IL (US)

( * ) Notice: Subject to any disclaimer, the term of this patent is extended or adjusted under 35 U.S.C. 154(b) by 1100 days.

(21) Appl. No.: 16/141,027

(22) Filed: Sep. 25, 2018

(65) Prior Publication Data

US 2020/0093651 A1    Mar. 26, 2020

(51) Int. Cl.
*A61F 13/49* (2006.01)
*A61F 13/84* (2006.01)
*A61F 13/68* (2006.01)

(52) U.S. Cl.
CPC .......... *A61F 13/49* (2013.01); *A61F 13/4906* (2013.01); *A61F 13/68* (2013.01); *A61F 13/84* (2013.01); *A61F 2013/49076* (2013.01); *A61F 2013/49077* (2013.01); *A61F 2013/8497* (2013.01)

(58) Field of Classification Search
CPC .................. A61F 13/68; A61F 13/4906; A61F 2013/49077; A61F 2013/49076; A61F 13/66; A61F 13/74–78
See application file for complete search history.

(56) References Cited

U.S. PATENT DOCUMENTS

| | | | |
|---|---|---|---|
| 5,876,394 A * | 3/1999 | Rosch | A61F 13/565 604/393 |
| 6,547,774 B2 * | 4/2003 | Ono | A61F 13/49009 604/385.29 |
| 6,578,210 B2 | 6/2003 | Erickson | |
| 6,652,503 B1 | 11/2003 | Bradley | |
| 6,928,680 B1 | 8/2005 | Cai et al. | |
| 6,981,289 B2 | 1/2006 | Mueller et al. | |
| 7,537,586 B2 | 5/2009 | Kline et al. | |
| 7,833,212 B2 | 11/2010 | Magee et al. | |

(Continued)

FOREIGN PATENT DOCUMENTS

KR    1020120006168 A    1/2012

OTHER PUBLICATIONS

Notification of Transmittal of the International Search Report and the Written Opinion of the International Searching Authority, or the Declaration for PCT Application No. PCT/US2019/050765 (dated Dec. 27, 2019).

(Continued)

*Primary Examiner* — Susan S Su
(74) *Attorney, Agent, or Firm* — Gurr Brande & Spendlove, PLLC.; Robert Dan Spendlove

(57) ABSTRACT

An apparatus for assisting a caregiver with aligning an absorbent article chassis and side panels with a supine wearer's hips, spine and leg opening. The apparatus includes a complementary mechanical fastener portion for engaging with an absorbent article complementary mechanical fastener portion. To align the apparatus and absorbent article assembly, a caregiver, utilizing a grasping element positions the assembly beneath a supine wearer with fewer incidents of ripping and tearing of absorbent article side panels and fasteners prior to application.

20 Claims, 15 Drawing Sheets

(56) References Cited

U.S. PATENT DOCUMENTS

| | | |
|---|---|---|
| 7,863,497 B2 | 1/2011 | Magee et al. |
| 8,037,561 B2 | 10/2011 | Austwick et al. |
| 8,039,685 B2 | 10/2011 | Mason, Jr. et al. |
| 8,167,862 B2 | 5/2012 | Digiacomantonio et al. |
| 8,304,597 B2 | 11/2012 | Hughes et al. |
| 8,313,473 B2 | 11/2012 | Datta |
| 8,395,013 B2 | 3/2013 | Digiacomantonio et al. |
| 8,491,559 B2 | 7/2013 | Digiacomantonio et al. |
| 8,492,608 B2 | 7/2013 | Magee et al. |
| 8,661,589 B2 | 3/2014 | Schambon |
| 8,716,548 B2 | 5/2014 | Magee et al. |
| 8,763,182 B2 | 7/2014 | Schambon |
| 9,155,343 B1 | 10/2015 | Robbins |
| 9,532,914 B1 | 1/2017 | Nichols |
| 9,907,412 B2 | 3/2018 | Perry |
| 10,058,193 B2 | 8/2018 | Karavias |
| 10,165,802 B2 | 1/2019 | Clouse et al. |
| 2002/0022820 A1 | 2/2002 | Kline et al. |
| 2003/0158532 A1 | 8/2003 | Magee et al. |
| 2004/0025250 A1 | 2/2004 | Bezalel |
| 2004/0158218 A1 | 8/2004 | Mueller et al. |
| 2005/0022291 A1* | 2/2005 | Coates ............. A61F 13/492/400 |
| 2005/0131381 A1* | 6/2005 | Kuen ............... A61F 13/5633 604/396 |
| 2005/0137564 A1 | 6/2005 | Strannemalm |
| 2005/0278855 A1 | 12/2005 | Welch |
| 2008/0004585 A1 | 1/2008 | McCusker et al. |
| 2012/0090094 A1 | 4/2012 | Whitlock Petersen |
| 2014/0005621 A1* | 1/2014 | Roe ............... A61F 13/5644 604/365 |
| 2014/0200542 A1 | 7/2014 | Magee et al. |

OTHER PUBLICATIONS

International Search Report for PCT Application No. PCT/US2019/050765 (dated Dec. 27, 2019).

* cited by examiner

APPARATUS AND METHOD FOR APPLICATION OF ABSORBENT ARTICLE

FIELD OF THE INVENTION

Embodiments of the present invention relate primarily to an apparatus to aid caregivers in the application and positioning of absorbent articles around a wearer in a supine position.

BACKGROUND OF THE INVENTION

Disposable absorbent articles are well known in the prior art and have many uses. Whether intended for infants, children, adults or the elderly, disposable pads, napkins, diapers, training pants, briefs, underwear, incontinence articles, and the like are intended to absorb and retain body discharges. As used herein, "absorbent article" will refer to all these examples.

Conventional diaper style absorbent articles typically include a chassis having first waist portion, a second waist portion, and a crotch region there between. The first and second waist portions may include a plurality of side panels corresponding with a wearer's hip region, the side panels, which when coupled together form first and second leg openings and a waist opening. The side panels are often releasably connected about the hips of the wearer by conventional fasteners such as adhesive and cohesive tape fasteners or hook and loop type fasteners, magnets, etc. Conventional fasteners typically include a pair of fasteners, located on the outermost corners of the absorbent article second waist portion and a pair of complimentary fasteners located on the first waist portion.

Absorbent articles are commonly misapplied due to the awkward positioning of the wearer (supine position) relative to a caregiver (standing, bending, reaching), restless movement of the wearer, height of the application/changing surface relative to the height and reach of the caregiver, and/or weight of the wearer relative to the strength of a caregiver.

Problems associated with the application of absorbent articles can be exacerbated when an absorbent article does not easily stay in position during the application process. For example, absorbent articles often include elastic leg cuffs which need to be flattened or straightened prior to application. Owing to the elastic properties of leg cuffs, absorbent articles have a tendency to fold or roll back into an unflattened condition.

In some instances, the wearer cannot assist a caregiver with the application of the absorbent article. Infants, infirmed and post-operative individuals may not be able to raise their hips and buttocks off of absorbent article application/changing surface. In some instances, a wearer may be restless and fidgety, frustrating the efforts of a caregiver to correctly align an absorbent article on the wear's body. Such restless motion by the wearer can also require a caregiver to devote one hand to maintaining the wearer's body on the absorbent article application/changing surface, while simultaneously devoting another hand to the alignment and application of an absorbent article leading to an improperly fitted absorbent article about a wearer's body.

When an absorbent article is improperly fitted to a wearer, the result may include an uneven fit (e.g., one leg open gaps while another leg opening is overly tight) and incorrect placement of securement fasteners/devices. Further, an improperly applied absorbent article can lead to leakage of body discharges from too low placement around a wearer's hips, a gapping leg opening, skin irritation and/or general discomfort where a leg opening is overly tight.

Ideally, a caregiver is encouraged to apply an absorbent article on a wearer so that the first and second waist portions, side panels, and consequently, first and second leg openings are substantially aligned with each other. To assist with proper alignment, some absorbent articles, such as applicant's own Mills U.S. Pat. Nos. 9,750,650, 8,920,399, 8,419,703 and 8,241,263 teach absorbent articles including visual sizing indicators and fastener target strips to ensure both application of a correctly sized article and alignment of the article relative to a wearer.

When applying an absorbent article under a supine wearer, a caregiver may have to apply significant force to a side panel and/or fastener in order to position an absorbent article beneath a wearer and to correctly align the various components of an absorbent article relative to specific body portions of a wear. Pulling forces, localized along one edge of the absorbent article may therefore cause, for example, a tear in the side panel/fastener being pulled rendering the absorbent article unsuitable for use.

There is therefore a need for a device to facilitate proper alignment and application of an absorbent article about a wearer without placing unnecessary and damaging strain on the absorbent article structures.

BRIEF SUMMARY OF THE INVENTION

Embodiments of the invention provide an apparatus upon which an absorbent article is releasably affixed. The apparatus is sized and shaped to provide visual signals to a caregiver for the proper alignment of both the absorbent article and apparatus relative to a wearer's body. The apparatus may also include visual indicia to further aid in alignment. The apparatus may also include handle structures for a caregiver to grasp to aid in movement, positioning and alignment of the assembly under a supine wearer's buttock and hips, spine and leg opening without placing unnecessary stress or strain on the absorbent article.

BRIEF DESCRIPTION OF THE DRAWINGS

The various aspects, features and advantages of the disclosure will become more fully apparent to those having ordinary skill in the art upon careful consideration of the following Detailed Description thereof with the accompanying drawings described below.

Figure 1:
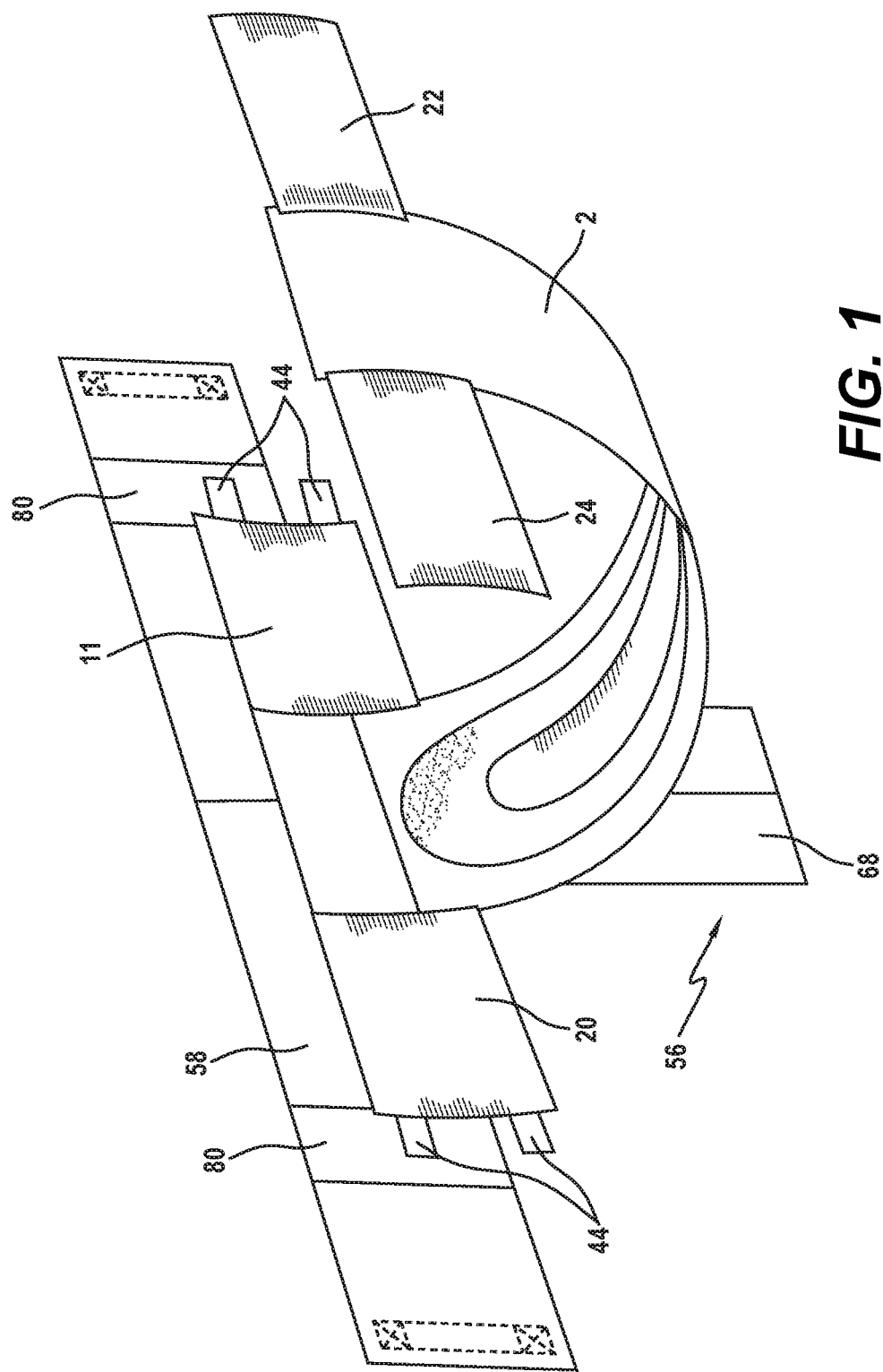
FIG. 1 is an exploded perspective view of an embodiment of an absorbent article application mat and absorbent article.

While embodiments of the invention are susceptible to various modifications and alternative forms, specific embodiments have been shown by way of example in the drawings and will be described in detail herein. Furthermore, components from one embodiment can be used in other non-exclusive embodiments. It should be understood however, that the invention is not intended to be limited to the particular forms disclosed. Rather, the invention will cover all modifications, equivalents, and alternatives falling within the spirit and scope of the invention.

DETAILED DESCRIPTION

Embodiments of the invention are now described in detail. Referring to the drawings, like numbers indicate like parts throughout the views. As used in the description herein and throughout the claims, the following terms take the meanings explicitly associated herein, unless the context clearly indicates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions.

As used herein, the following terms have the following meanings:

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

"Connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end user.

"Integral" is used to refer to various portions of a single unitary element rather than separate structures bonded to or placed with or placed near one another.

These terms may be defined with additional language elsewhere in the specification.

It should be observed that the embodiments reside primarily in the combinations of apparatus components and method steps. Accordingly, the apparatus components and the method steps have been represented (where appropriate) by conventional symbols in the drawings, showing only those specific details that are pertinent to understanding the embodiments of the present invention so as not to obscure the disclosure with details that will be readily apparent to those of ordinary skill in the art having the benefit of the description herein.

Embodiments disclosed herein are directed to an apparatus for application of absorbent articles onto users who are in a supine position and require a caregiver to apply absorbent articles. Further, embodiments disclosed herein are directed to absorbent article users in general without limitation given to the age, weight, or size of the wearer.

Disposable absorbent articles 2 as illustrated by FIG. 2A-2D and as described herein generally include several layers: a moisture-pervious inner layer 4, a moisture-impervious outer layer 8 substantially co-extensive with the inner layer 4 and one or more absorbent layers 6 interposed between the inner layer 4 and the outer layer 8.

Absorbent article 2 may generally include a chassis 10 having a first portion 12, a second portion 14 and a center portion 16 connected there between and plurality of side panels 18, 20, 22, 24. As used herein, the first portion 12 will generally describe the portion of the absorbent article 2 oriented over the front of a wearer and the second portion 14 will generally describe the portion of the absorbent article 2 oriented over the rear of a wearer. Such orientation is not intended to be limiting and in other embodiments, the orientations may be reversed.

In the illustrated embodiment, the side panels 18, 20, 22, 24 may be separate elements attached to the chassis 10 first portion 12 and second portion 14 along side edges 26, 28 of the first 12 and second portions 14. In this illustrated embodiment there are four side panels comprising a first side panel 18, a second side panel 20, a third side panel 22 and a fourth side panel 24. While four side panels are illustrated, it should, however, be recognized that other embodiments may be configured with more or fewer side panels. Alternatively, the side panels may be integrally formed with the first and second chassis portions.

In accordance with the embodiments of FIGS. 2A-2D, the chassis has a width $C_W$ 30, 130, 230, 330. The plurality of side panels have a width $S_W$ 32, 132, 232, 332, a length $S_L$ 34, 134, 234, 334, a distal edge portion 36, 136, 236, 336, a top edge portion 38, 138, 238, 338 and a lower edge portion 40, 140, 240, 340. The chassis width $C_w$ 30, 130, 230, 330 plus the first side panel width $S_w$ 32, 132, 232, 332 and the second side panel width $S_w$ 32, 132, 232, 332 have a combined width $SC_w$ 42, 142, 242, 342.

Adult incontinence absorbent articles may include two fasteners 44 per side panel to ensure both a tight fit around a wearer's waist as well as a tight or sealed gasket in the wearer's crotch area to prevent leakage. As illustrated, the first and second side panels, 18, 20 each include two fasteners 44. Fasteners can be configured to operatively couple the first side 18 panel to the third side panel 22 and/or to anywhere along the first portion 12 outer layer 8 and the second side panel 20 to the fourth side panel 24 and/or to anywhere along the first portion 12 outer layer 8.

While FIG. 2 depicts the first and second side panels 18, 20 as each including two fasteners 44, in some embodiments, the first and second side panels 18, 20 can include more or fewer fasteners 44. While FIG. 2 depicts fasteners 44 sized and shaped a particular way, in other embodiments, fasteners can be a different size and/or shape. While FIG. 2 depicts fasteners 44 extending beyond the side panel distal edge portions 36, in other embodiments, the placement of the fasteners relative to the side panels may be different, e.g., entirely within a perimeter of a side panel.

The types of fasteners may include pressure sensitive adhesive or cohesive tape, or other adhesive materials, tab members having an adhesive on one side, hook and loop, snaps, hook and eye, magnets or other suitable mechanical, complementary fastening structures for securing an absorbent article around a wearer.

Figure 2A:
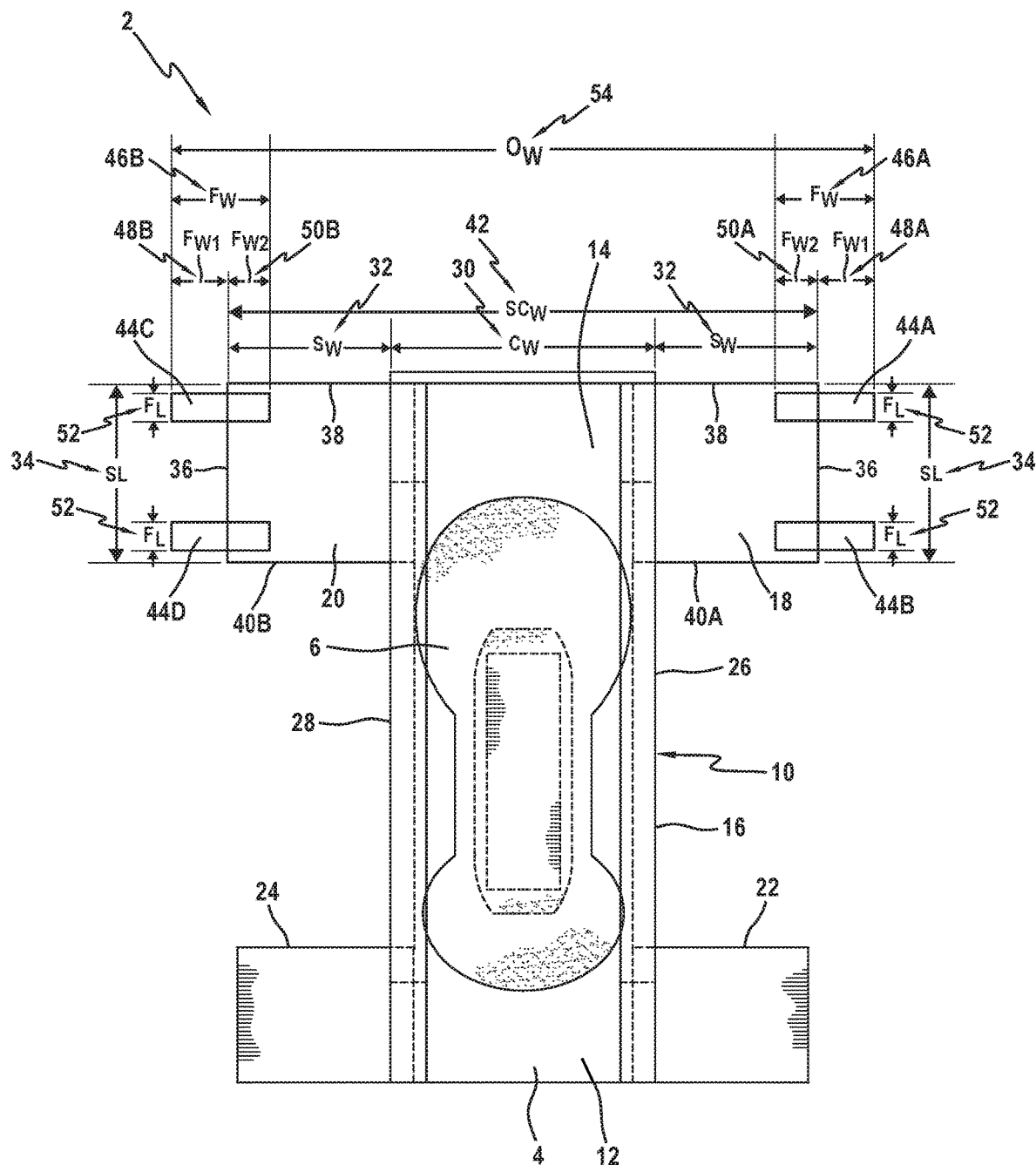
FIG. 2A is a plan views of an embodiment of an absorbent article.

In the embodiment of FIG. 2A, fasteners 44 have an overall width $F_W$ 46A, 46B, including a first width $F_{W1}$ 48A, 48B which extends beyond a distal edge portion 36 of a side panel 18, 20 width $S_W$ 32 and a second width $F_{W2}$ 50A, 50B positioned in the vicinity of a side panel 18, 20 distal edge portion 36. In addition, fasteners 44 have an overall length $F_L$ 52.

Figure 2B:
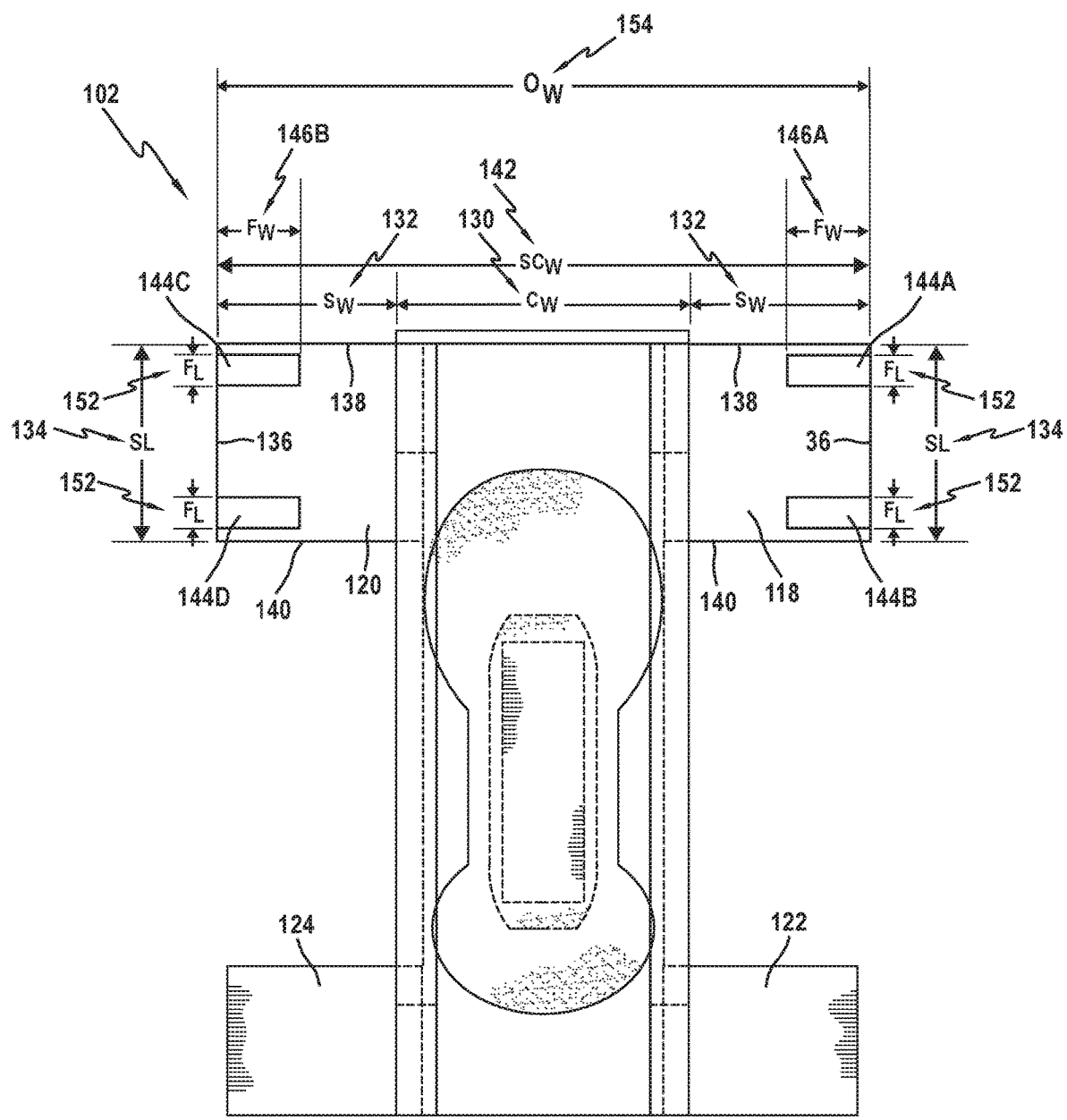
FIG. 2B is a plan views of a further embodiment of an absorbent article.

In the embodiment of FIG. 2B, a fastener 144 overall width $F_W$ 146A, 146B can be positioned along a side panel 118, 120 distal edge portion 136. In addition, fasteners 144 have an overall length $F_L$ 152.

Figure 2C:
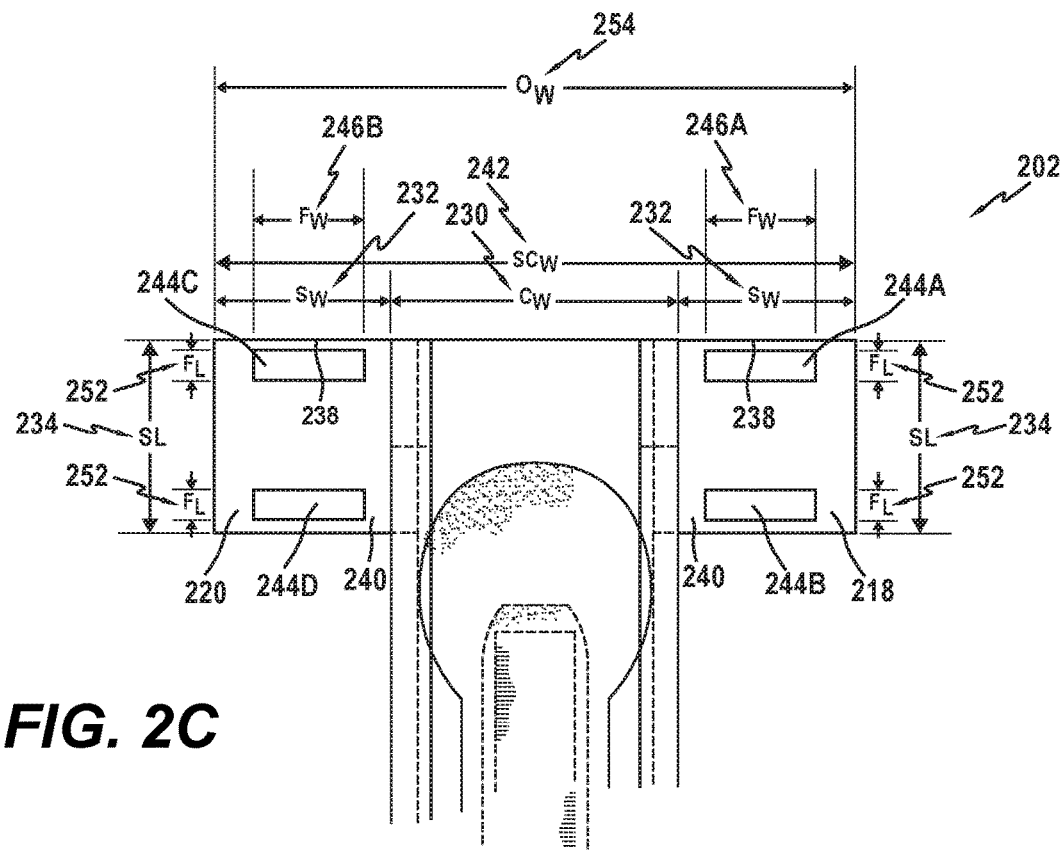
FIG. 2C is a partial plan views of a further embodiment of an absorbent article.

In the embodiment of FIG. 2C, the overall width $F_W$ 246A, 246B of a fastener 244 is positioned in spaced relation within a side panel 218, 220 perimeter. In addition, fasteners 244 have an overall length $F_L$ 252.

Figure 2D:
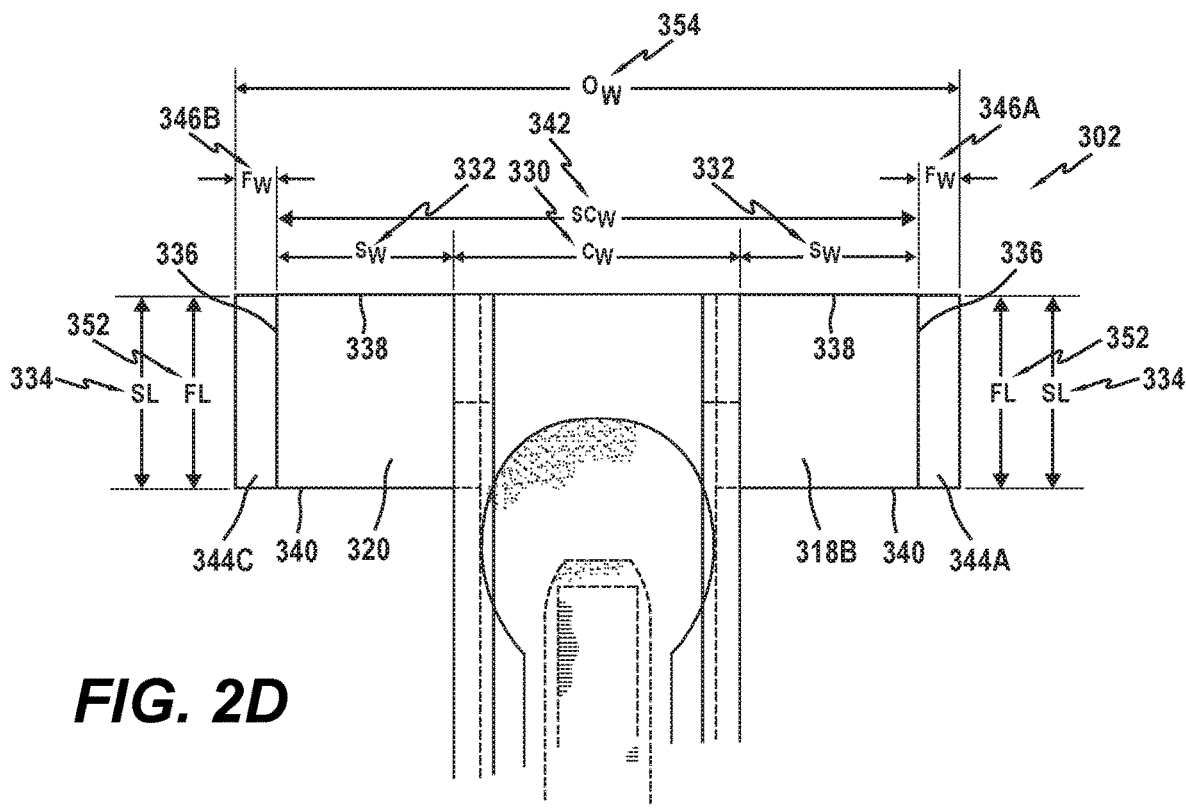
FIG. 2D is a partial plan views of a further embodiment of an absorbent article.

In the embodiment of FIG. 2D, a fastener overall width $F_W$ 346A, 346B may extend entirely beyond a side panel 318, 320 distal edge portion 336. In addition, fasteners 344 have an overall length $F_L$ 352

In an embodiment a fastener length $F_L$ may the substantially equal to, less than or greater than a side panel length $S_L$.

In accordance with the embodiments of FIGS. 2A-2D an absorbent article 2, 102, 202, 302 has an overall width $O_W$ 54, 152, 254, 354 which represents the sum total of the laterally extending absorbent article elements. As illustrated in the embodiment of FIG. 2A, the overall width $O_W$ 54 is the sum of a fastener width $F_{W1}$ 48A, the combined side panel and chassis widths $SC_W$ 42 and a second fastener width $F_{W1}$ 48B. By contrast, as illustrated in the embodiments of FIGS. 2B and 2C, the overall width $O_W$ 154, 254 is the sum of the combined side panel and chassis widths $SC_W$ 142, 242. In the embodiment of FIG. 2D, the overall width $O_W$ 354 is the sum of a fastener width, $F_W$ 346A, combined side panel and chassis widths $SC_W$ 342 and a second fastener width $F_W$ 346B.

In accordance with the various embodiments, the apparatus 56 is a tool for use by caregivers to assist with ensuring proper alignment of an absorbent article 2 on a wearer while the wearer is in a supine position on an absorbent article application/changing surface, such as a bed or changing table, mat or pad. In accordance with the various embodiments, use of the apparatus 56 improves the functionality of an absorbent article 2 by helping to ensure that a central longitudinal axis of absorbent layer 6 is aligned with a wearer's spine and leg opening while also helping to position side panels 18, 20, 22, 24 around a wearer's waist and hips. Symmetrical alignment of side panels 18, 20, 22, 24 and fasteners 44 helps to ensure that the absorbent article 2 first and second leg openings are substantially similar so as to avoid gapping and leaking where one leg opening is greater than another leg opening. Similarly, where one leg opening is smaller than a second opening, the leg opening can constrict around a wearer's leg leading to skin irritation or other discomfort.

Figure 3:
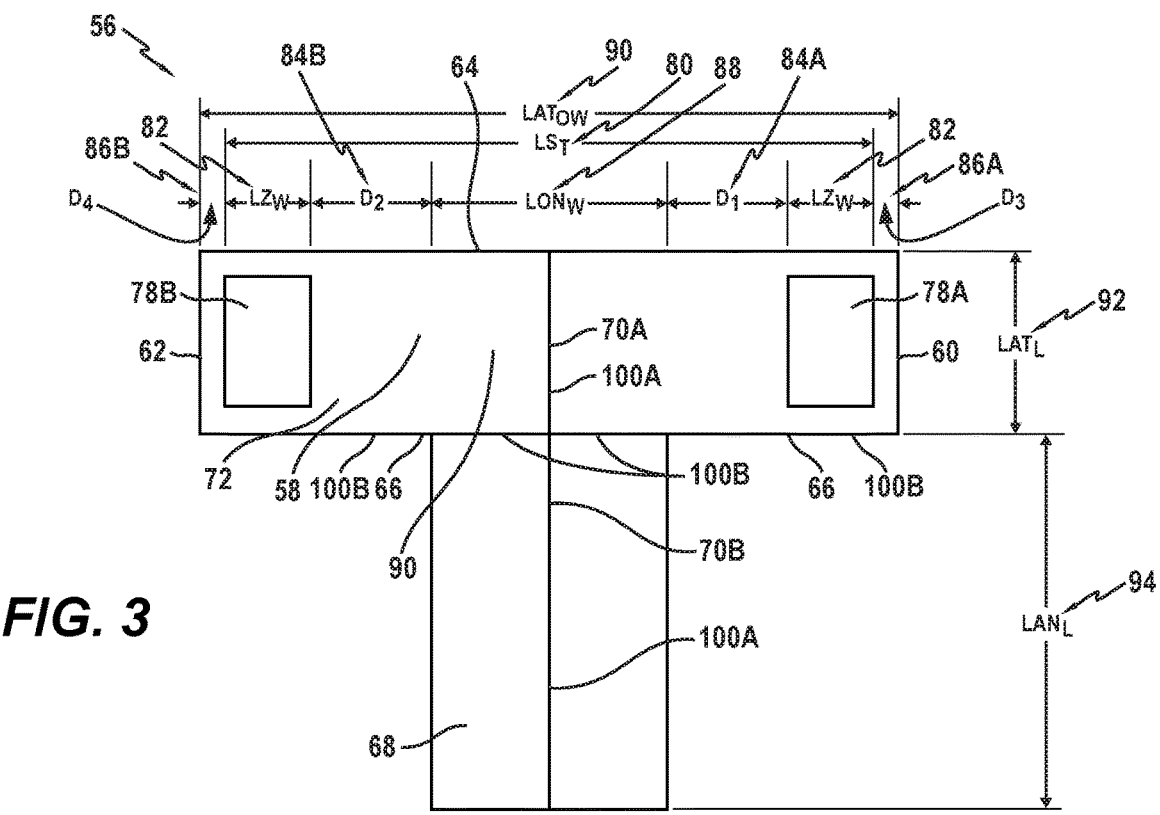
FIG. 3 a plan view of a first surface of an embodiment of an absorbent article application mat and attachment zone.
Figure 4:
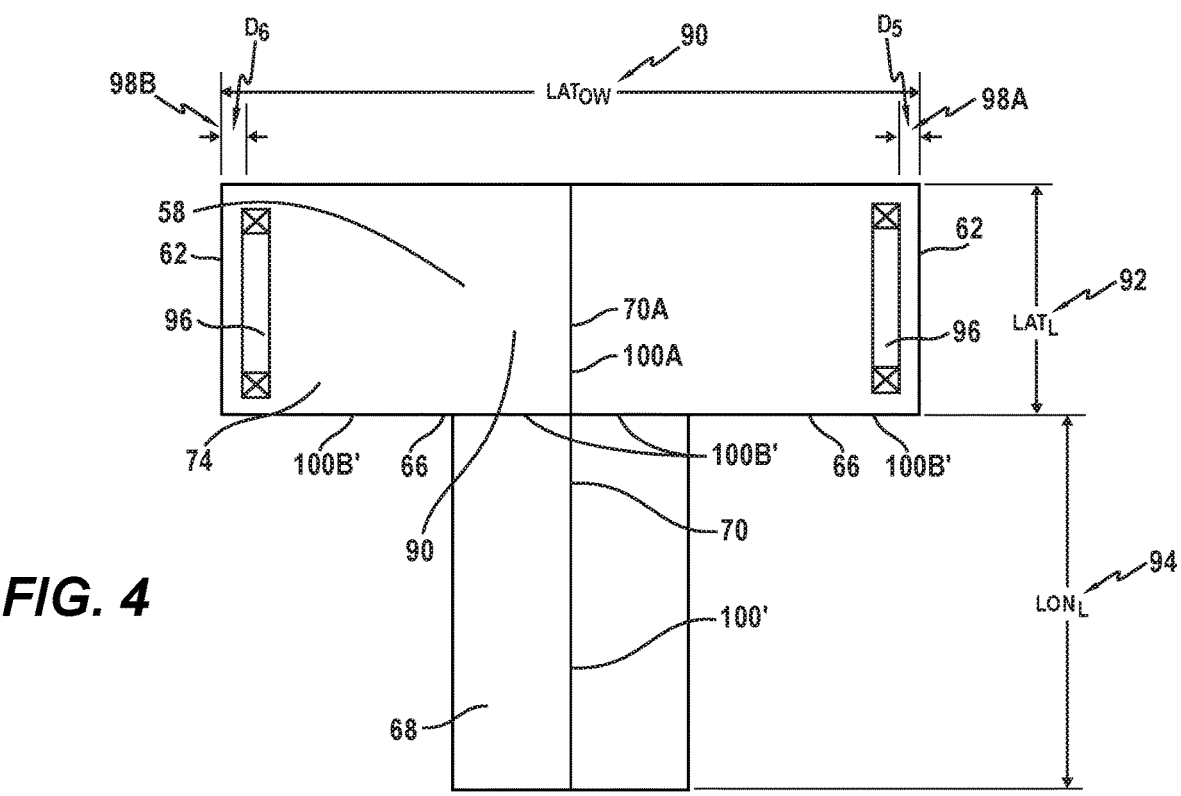
FIG. 4 is a plan view of a second surface of an embodiment of an absorbent article application mat including a grasping element.
Figure 25:
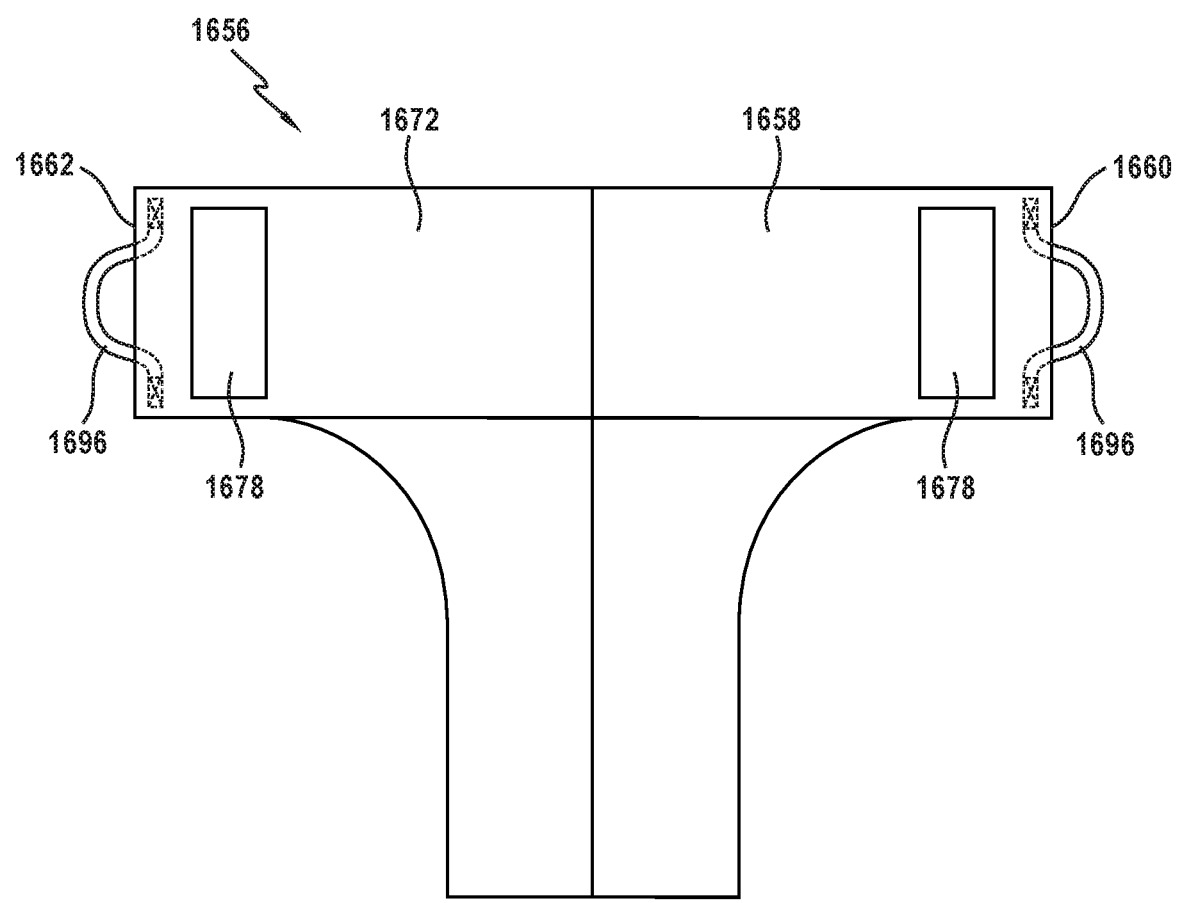
FIG. 25 is a plan view of an embodiment of an absorbent article application mat.

While a generally "T" shaped apparatus 56 is illustrated in the embodiments of FIGS. 1, and 3-4, other embodiments illustrate alternative form factors. For example, the apparatus may have a silhouette that is similar to the silhouette of an absorbent article. The embodiment of FIG. 25 illustrates an apparatus 1656 with a generally "T" shape structure that includes a curvature that may follow a curvature of an absorbent article leg opening, and FIG. 27 illustrates an apparatus 1856 including an "I" or hourglass shaped structure that generally corresponds with the shape of an absorbent article. The "I" shape of FIG. 27 is shown constructed of elements having straight edges meeting at right angles. However, it will be understood that the apparatus may employ curved edges such as illustrated in FIG. 25, resulting in an apparatus having a more hourglass shaped profile. Alternatively, other non-limiting form factors include a rectangular apparatus 1756 (FIG. 26) or elliptical; a triangular apparatus 1956 (FIG. 28); a pentagonal apparatus 2056 (FIG. 29); and a kite apparatus 2156 (FIG. 30). Other appropriate shapes may be used as would be understood by one of ordinary skill in the art.

In accordance with the embodiments of FIGS. 3 and 4, the apparatus 56 "T" shaped structure includes a laterally extending element 58 including first and second lateral distal ends 60, 62 and upper and lower edge portions 64, 66. The apparatus 56 "T" shaped structure further includes a longitudinally extending element 68, substantially perpendicular to the lateral element 58 and extending from the lateral element 58 lower edge portion 66. The laterally extending 58 element includes a central longitudinal axis 70A. Similarly, the longitudinally extending 68 element includes a central longitudinal axis 70B. In a preferred embodiment, the central longitudinal axis 70A of the laterally extending element 58 and the central longitudinal axis 70B of the longitudinally extending element 68 are substantially aligned.

The laterally extending element 58 and the longitudinally extending element 68 may be integrally formed or may be separate components which are joined together.

The apparatus 56 includes first and second surfaces 72, 74. The first surface 72 may be a top, body facing surface and the second surface 74 may be a bottom surface which faces the application/changing surface, such as a bed or changing table. In another embodiment, the surfaces may be reversed. In an embodiment, the first and second surfaces 72, 74 are at least partially coterminous.

The first surface 72 may be constructed from microfiber, other soft touch natural or synthetic material, or other appropriate materials The second surface 74 may be constructed from nylon, biaxially-oriented polyethylene terephthalate (BoPET) (MYLAR), flashspun high-density polyethylene (TYVEK) or other slick surfaced, low friction, natural or synthetic material, or other appropriate materials.

In an embodiment the apparatus 56 includes a substantially narrow profile so as to be largely unnoticeable when combined with an absorbent article and positioned beneath a wearer.

In an embodiment the apparatus 56 is flexible in every direction. In alternative embodiments, the apparatus 56 is semi-flexible, semi-rigid or rigid. In an embodiment the apparatus 56 is at least one of flexible, semi-flexible, semi-rigid, and rigid. In an embodiment, the apparatus 56, whether flexible, semi-flexible, semi-rigid or rigid, includes sufficient structure to maintain a substantially flat, normal condition after engaging with an absorbent article. That is, when the apparatus 56 engages with absorbent article 2, any elastic elements of absorbent article 2 will not cause apparatus 56 to bunch or fold.

Figure 17:
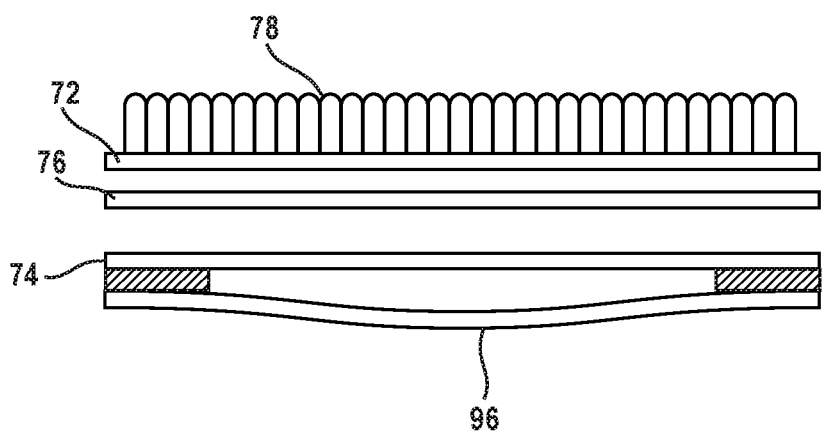
FIG. 17 is a partially exploded side view of an embodiment of absorbent article application mat, including an attachment zone and grasping element.

As illustrated in the embodiment of FIG. 17, one or more interfacing layers 76 may be positioned between the first and second surfaces 72, 74. In an embodiment, the interfacing layer 76 may extend over at least a portion of an area of at least one of the first and second surface 72, 74. In an embodiment, the interfacing layer 76 may be co-extensive with at least one of the first and second surfaces 72, 74. In an embodiment, the interfacing layer 76 may be a woven or non-woven material, fusible or non-fusible, paper, cardboard, film or poly material, natural or synthetic, or other material suitable for adding body to and giving support to the structure of the first and second surfaces 72, 74. In an embodiment, interfacing may be attached to at least one of the first and second surfaces 72, 74. In an embodiment, interfacing may not be attached to either the first or second surfaces 72, 74. In an embodiment, interfacing may be a padding layer. In an embodiment interfacing may be an absorbent material.

In an embodiment, the first and second surfaces 74, 76 are attached together by at least one of adhering, bonding, embossing, stitching or other suitable technique. In an embodiment, the method of attachment may be continuous or intermittent. In an embodiment, the first and second surfaces 72, 74 are attached along a perimeter of the joined surfaces. In an embodiment, the first and second surfaces 72, 74 are attached in a pattern extending over an area of the first and second surfaces 72, 74. In an embodiment a pattern of attachment may be linear, circular, intersecting, random or a combination of patterns. In an embodiment, the first and second surfaces 72, 74 are attached along a perimeter of the joined surfaces and over an area of the first and second surfaces.

The laterally extending element has an overall width $LAT_{OW}$ 90 and a length $LAT_L$ 92. The longitudinally extending element has a width $LON_W$ 88 and a length $LON_L$ 94.

In accordance with the embodiment of FIG. 3, the first surface 72 includes landing zones 78A, 78B positioned in the vicinity of each of the first and second lateral element distal ends 60, 62. In a preferred embodiment the apparatus 56 landing zone 78A, 78B will include a mechanical fastener structure which is complementary to the fastening structure 44 of an absorbent article 2, that is, the apparatus 56 landing zone 78A, 78B will include the structure of one portion of a complementary fastener that is opposite from the fastening structure 44 of the absorbent article 2 second portion 14. Said differently, if the absorbent article 2 second portion 14 fastener 44 includes a male portion of a hook and loop structure, then the apparatus 56 landing zone 78A,78B will include a complementary female portion of a hook and loop structure.

Other non-limiting landing zone examples may include tape adhesive, a cohesive, and magnetic landing zones, a landing zone area constructed from the same material as an outer layer of an absorbent article or a landing zone area of reinforce material that can both receive an absorbent article fastener, and subsequently have the absorbent article fastener removed from the landing zone without damaging either the fastener or the landing zone. The area of reinforced material may include a plastic film or BoPET.

In an embodiment, the landing zone 78 may be applied to or affixed to the apparatus 56 by at least one of adhering, bonding, embossing, stitching or other suitable technique suitable. In an alternative embodiment, the landing zone 78 may be integral to the apparatus.

Figure 13:
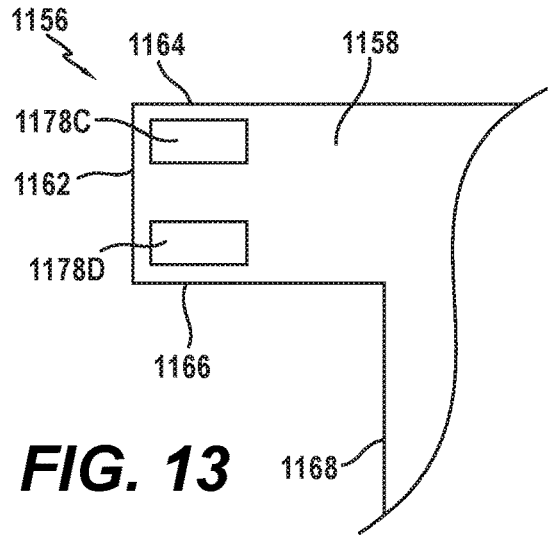
FIG. 13 is a partial plan view of an embodiment of attachment zones for an absorbent article application mat.
Figure 14:
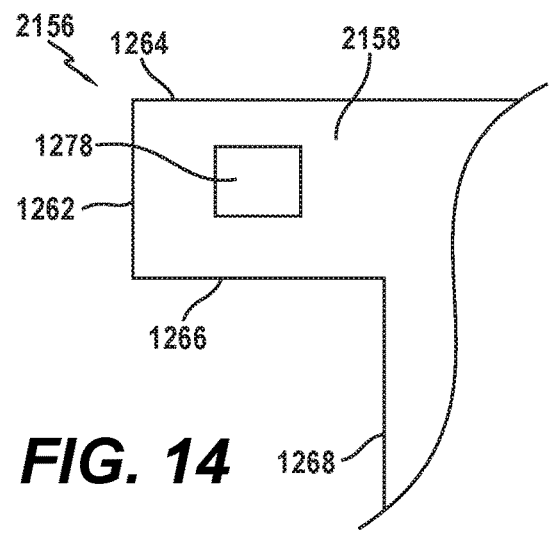
FIG. 14 is a partial plan view of an alternative embodiment of an attachment zone for an absorbent article application mat.
Figure 15:
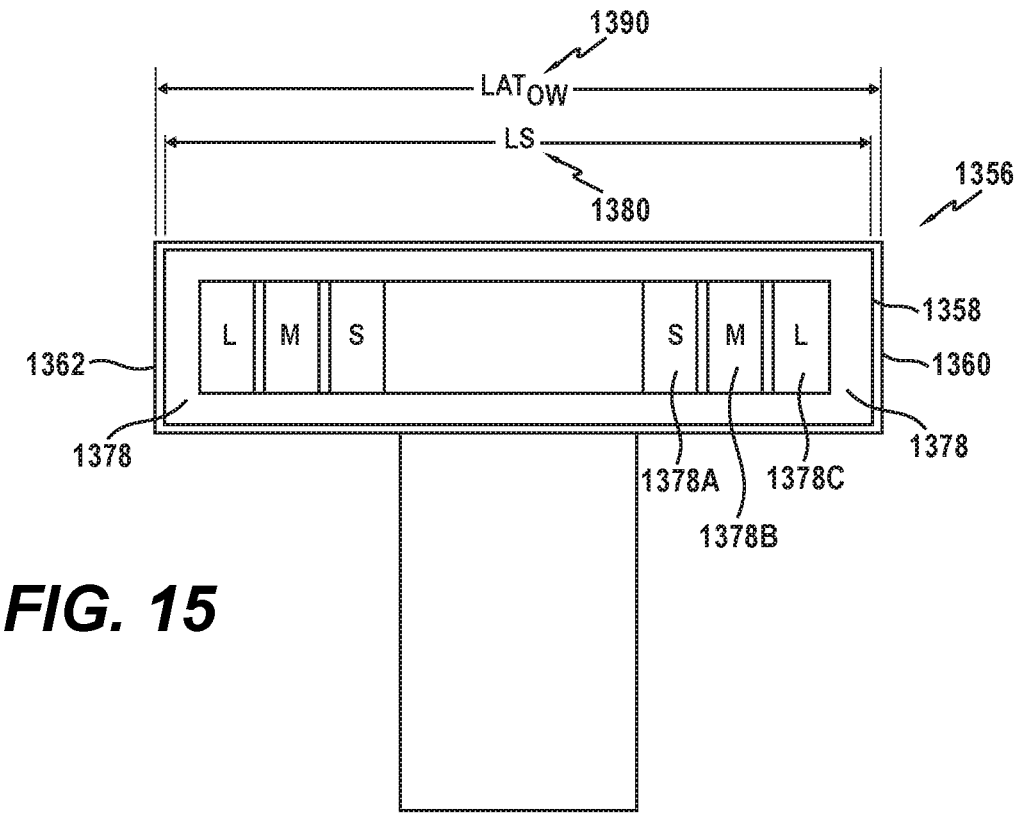
FIG. 15 is a plan view of an alternative embodiment of attachment zones for an absorbent article application mat.
Figure 16:
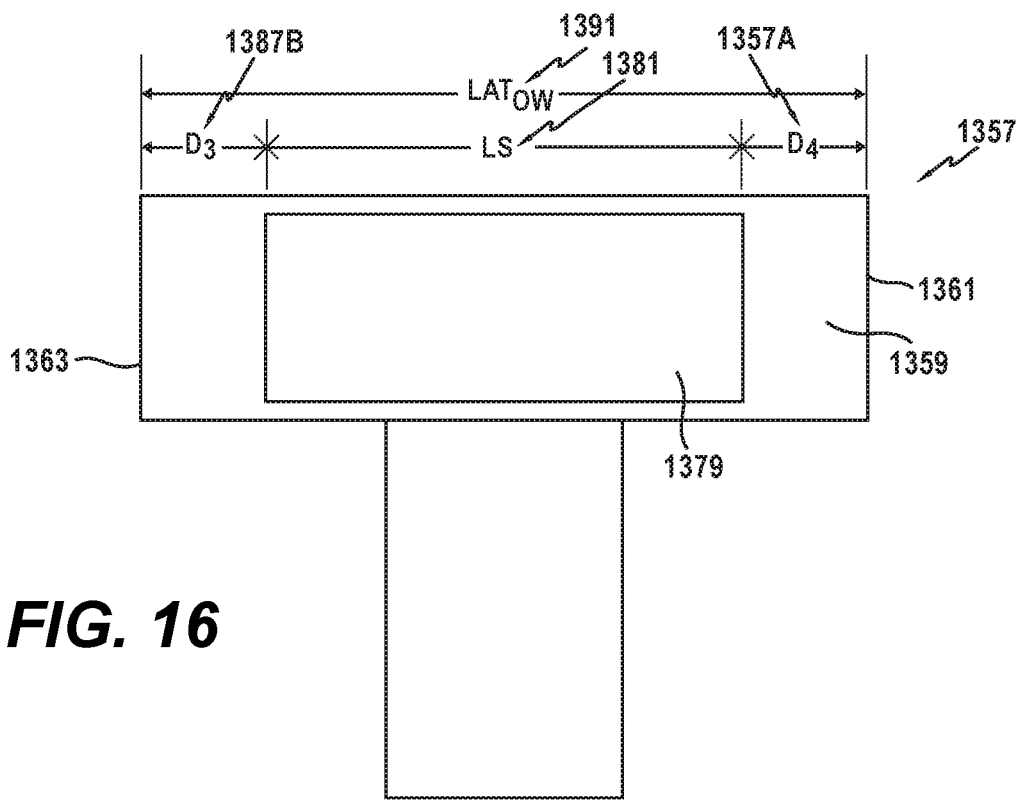
FIG. 16 is a plan view of an alternative embodiment of an attachment zone for an absorbent article application mat.

While the embodiment of FIG. 3 depicts a single, rectangular landing zone 78 at each of the lateral element distal ends 60, 62, in other embodiments, landing zones may be of a different quantity, size, shape and/or placement. By way of non-limiting example the apparatus 1156 of FIG. 13 illustrates two landing zones 1178 within a distal end 1162 of a laterally extending element 1158; the apparatus 1256 of FIG. 14 illustrates a single, square landing zone 1278 centrally positioned within a lateral element 1258; the apparatus 1356 of FIG. 15 illustrates a landing zone 1378 that generally substantially spans the laterally extending element 1358 forming a landing site 1380; and the apparatus 1357 of FIG. 16 illustrates a single central landing zone 1379 spanning a central portion of the laterally extending element 1359. Similar to apparatus 1356, apparatus 1357 includes a landing site 1381. In accordance with the embodiments of FIGS. 15 and 16 the landing site 1382, 1381 may receive fasteners 44 and a second portion 14 of an absorbent article 2. Said differently, the landing site 1382, 1381 is capable of releasably engaging with both absorbent article fasteners 44 and outer layer 8.

While the embodiments of FIGS. 13-14 illustrate partial views of various embodiments of laterally extending elements and associated landing zones, it is to be understood that the unillustrated opposite end of the various laterally extending elements and associated landing zones are mirror images of the illustrated portions.

In an embodiment, placement of one or more landing zones is not restricted to just the laterally extending element. In an embodiment, a landing zone may be positioned on both the laterally extending element and the longitudinally extending element. In a further embodiment one or more landing zones may be placed on each of a first surface and a second surface of the apparatus.

As illustrated, the landing zones 78 have a width $LZ_W$ 82. Each of the landing zones 78 may be positioned in the vicinity of lateral element first distal edge portions 60 separated by distance $D_3$ 86A and in the vicinity of lateral element second distal edge portion 62 separated by $D_4$ 86B. Each of the landing zones 78 may be further positioned in spaced relation to a central portion of the laterally extending element and separated by distances $D_1$ and $D_2$ 84A, 84B, the central portion being defined by a width of the longitudinally extending element $Lon_W$ 88. Accordingly, the laterally extending element overall width $Lat_{OW}$ 90 is defined by the sum of distances $D_1$, $D_2$, $D_3$, $D_4$ 84A, 84B, 86A, 86B, a width of the landing zones $LZ_W$ 82A, 82B and the width of longitudinally extending element $Lon_W$ 88.

In an embodiment, distances $D_1$ and $D_2$ are substantially equal. In an embodiment, distances $D_3$ and $D_4$ are substantially equal.

In an embodiment, the laterally extending element includes a landing site width LS, defined as a sum of distances $D_1$, $D_2$, a width of the landing zones $LZ_W$ and a width of longitudinally extending element $Lon_W$.

In the embodiment of FIG. 15, the laterally extending element overall width $Lat_{OW}$ 1390 and the landing site width LS 1380 may be substantially equal or nearly equal.

In the embodiment of FIG. 16, the laterally extending element overall width $Lat_{OW}$ 1391 is defined by the sum of distances $D_3$, $D_4$, 1387A, 1387B and a width of the landing site LS 1381.

In an embodiment, the laterally extending element overall width $Lat_{OW}$ 90 may be greater than an absorbent article overall width $O_W$ 54. In an alternative embodiment, the laterally extending element overall width $Lat_{OW}$ may be equal to an absorbent article overall width $O_W$.

In an embodiment, the landing site width LS may be greater than an absorbent article overall width $O_W$. In an alternative embodiment, the landing side width LS may be equal to an absorbent article overall width $O_W$.

In an embodiment, a length of the laterally extending element $Lat_L$ and a length of an absorbent article side panel $S_L$ are substantially equal. In alternative embodiments, a length of the laterally extending element $Lat_L$ may be greater than or less than a length of an absorbent article side panel $S_L$. In an embodiment, a length of the laterally extending element $Lat_L$ and a side panel fastener length $F_L$ are substantially equal. In alternative embodiments, a length of the laterally extending element $Lat_L$ may be greater than or less than a length of a side panel fastener length $F_L$.

In accordance with the embodiments of FIGS. 2A and 3, a landing zone width $LZ_W$ 82 and a fastener width $F_W$ 46 are substantially equal. In alternative embodiments, a landing zone width $LZ_W$ may be greater than or less than a fastener width $F_W$. In an embodiment, a width of the longitudinally extending element $Lon_W$ and a chassis width $C_W$ are substantially equal. In an alternative embodiment, a width of the longitudinally extending element $Lon_W$ may be greater than the chassis width $C_W$. In a further alternative, a width of the longitudinally extending element $Lon_W$ may be less than a chassis width $C_W$.

As illustrated in FIG. 4, the apparatus second surface includes a plurality of grasping 96 elements positioned in the vicinity of each of the lateral element first and second lateral distal ends 60, 62.

In an embodiment, grasping elements 96 are attached to the second surface 74 by at least one of adhering, bonding, stitching or other suitable techniques. In an embodiment, grasping elements 96 may be formed from a woven or non-woven material, natural or synthetic material. Non-limiting examples include: cording, ribbon, strapping, webbing, and the like. In an embodiment, the grasping elements may be elastic. In an embodiment, grasping elements may be rigid, semi-rigid, semi-flexible or flexible.

In an embodiment, grasping elements may be sized to receive at least one of a human finger, fingers, hand and the combination of a hand and wrist.

As illustrated in the embodiment of FIG. 4, grasping elements 96 may be positioned in the vicinity of each of the lateral element distal ends 60, 62, separated by a distance D5, D6 98A, 98B. In an embodiment, distances D5, D6 98A, 98B may be less than, substantially equal to or greater than distances D3, D4 86A, 86B.

Figure 5:
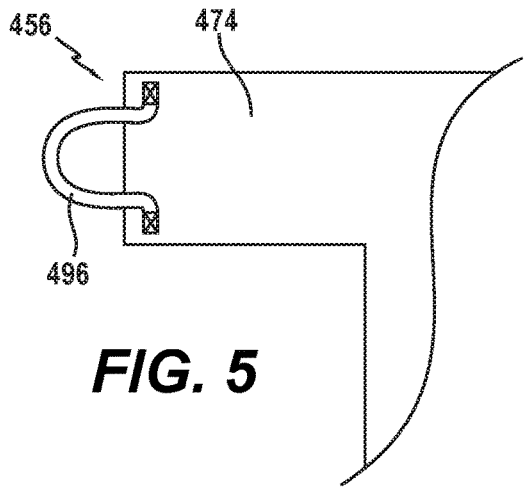
FIG. 5 is plan views of an embodiment of a grasping element for an absorbent article application mat.
Figure 7:
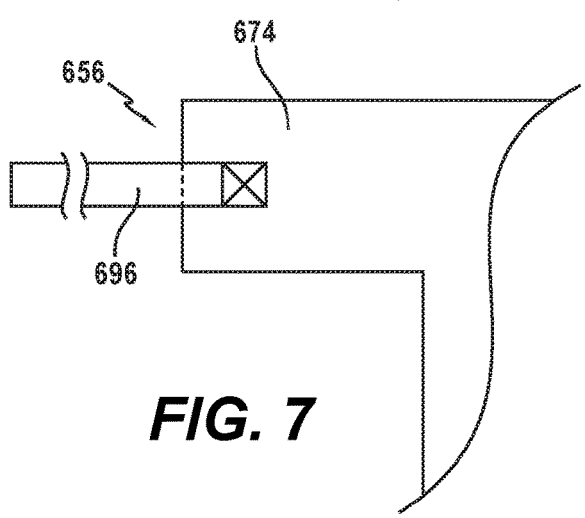
FIG. 7 is plan views of an alternative embodiment of a grasping element for an absorbent article application mat.
Figure 8:
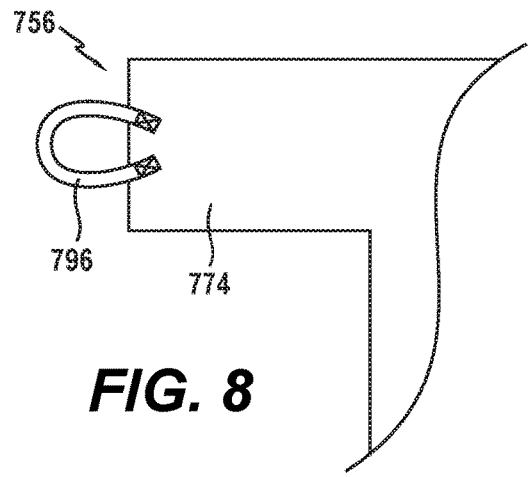
FIG. 8 is plan views of an alternative embodiment of a grasping element for an absorbent article application mat.
Figure 9:
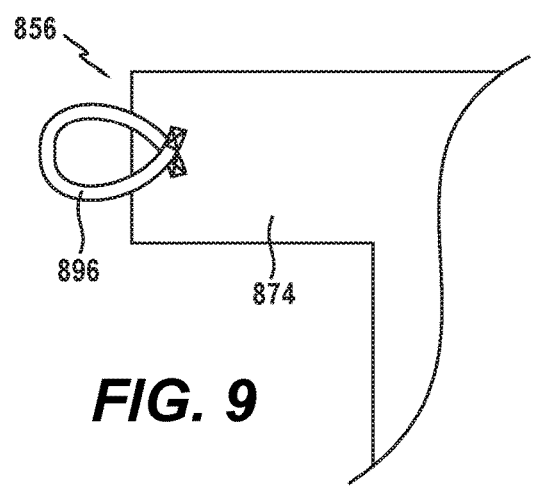
FIG. 9 is plan views of an alternative embodiment of a grasping element for an absorbent article application mat.
Figure 10:
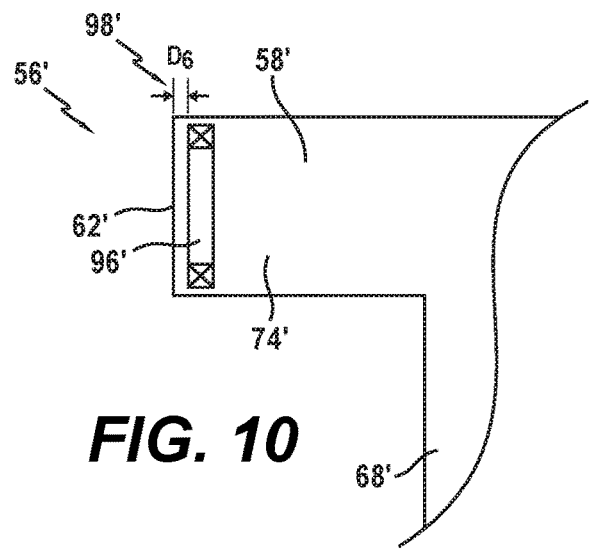
FIG. 10 is plan views of an alternative embodiment of a grasping element for an absorbent article application mat.
Figure 18:
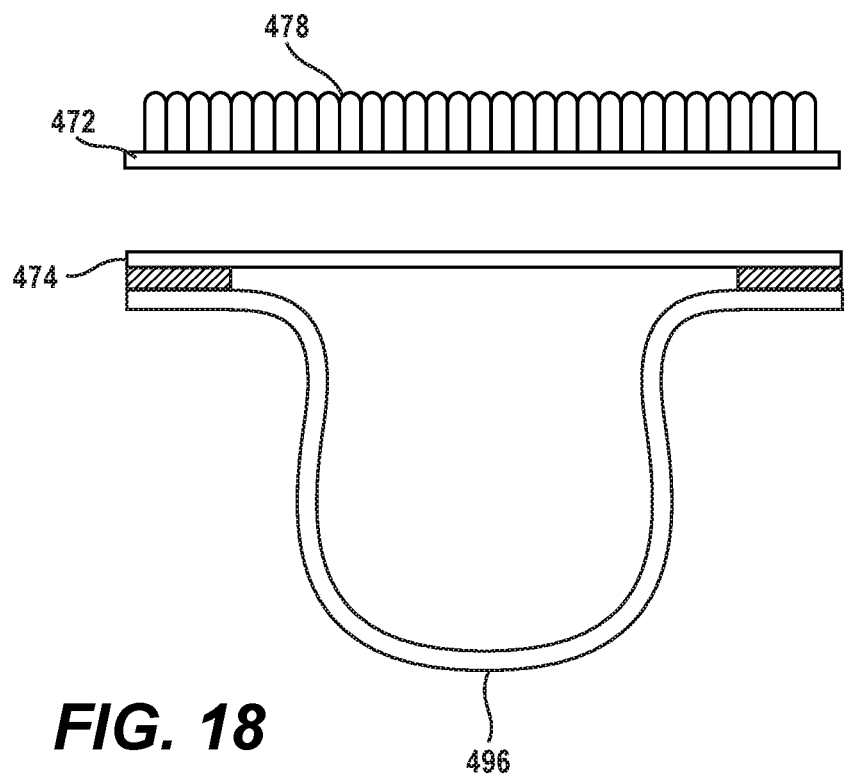
FIG. 18 is a partially exploded side view of an alternative embodiment of absorbent article application mat, including an attachment zone and grasping element.
Figure 19:
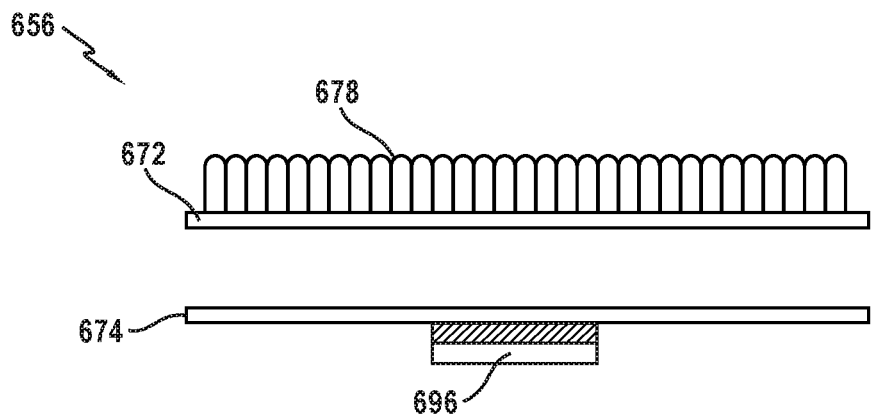
FIG. 19 is a partially exploded side view of an alternative embodiment of absorbent article application mat, including an attachment zone and grasping element.
Figure 20:
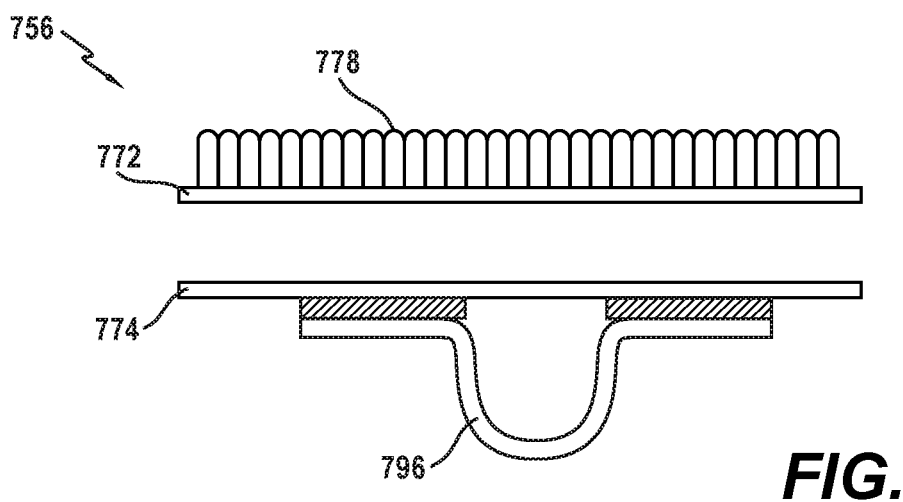
FIG. 20 is a partially exploded side view of an alternative embodiment of absorbent article application mat, including an attachment zone and grasping element.
Figure 21:
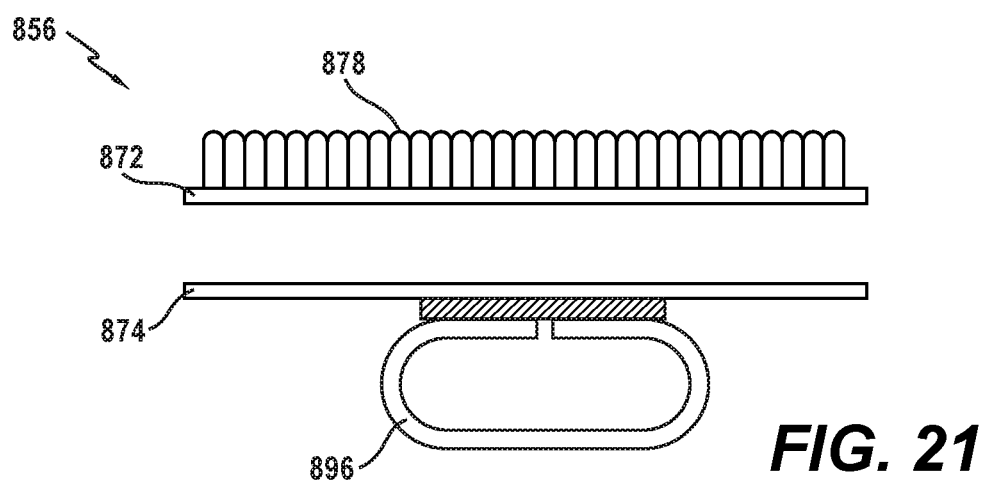
FIG. 21 is a partially exploded side view of an alternative embodiment of absorbent article application mat, including an attachment zone and grasping element.

As illustrated in the embodiment of FIG. 10, a grasping element 96' may be positioned along an edge portion of a lateral element distal end 62'. As illustrated FIG. 17, grasping elements 96, 96' of FIGS. 4 and 10 lay substantially flat against the apparatus second surface 56, 56'. In accordance with the embodiments of FIGS. 5 and 18, a grasping element 496 forms a loop. In accordance with the embodiments of FIGS. 7 and 19, a grasping element 696 may be a length of woven, non-woven, cording, ribbon, strapping or other suitable material that may be wrapped around a caregiver's hand or wrist prior to grasping. The grasping elements of the embodiments of FIGS. 8 and 20 are similar to the embodiments of FIGS. 5 and 18, except that end portions of the grasping element 796 material are more centrally positioned along the longitudinal distance of a lateral element. In accordance with the embodiments of FIGS. 9 and 21, grasping element 896 end portions may touch or overlap forming a loop of grasping element material. In each of the above identified embodiments, grasping elements may be affixed to the apparatus second surface. In an alternative embodiment, grasping elements may be affixed to the apparatus first surface.

Figure 11:
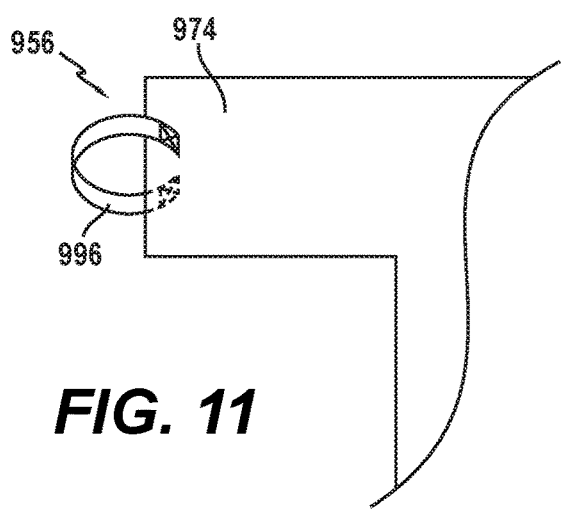
FIG. 11 is plan views of an alternative embodiment of a grasping element for an absorbent article application mat.
Figure 23:
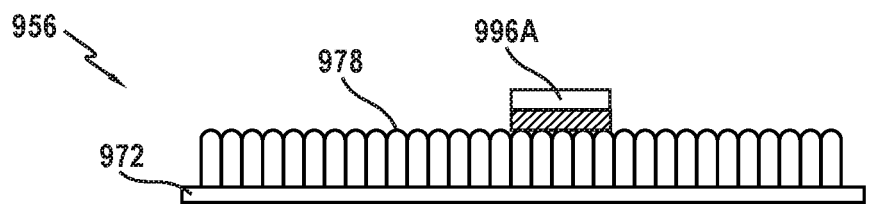
FIG. 23 is a partially exploded side view of an alternative embodiment of absorbent article application mat, including an attachment zone and grasping element.
Figure 24:
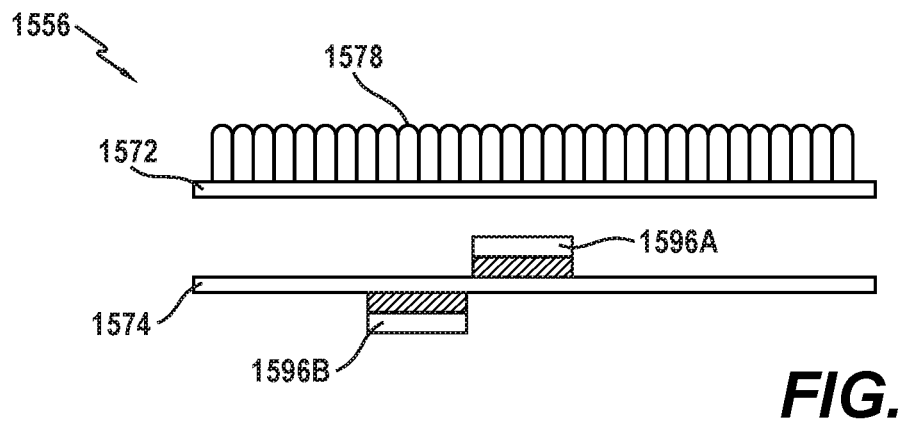
FIG. 24 is a partially exploded side view of an alternative embodiment of absorbent article application mat, including an attachment zone and grasping element.

In accordance with the embodiment of FIGS. 11 and 23, a grasping element first end 996A may be affixed to the apparatus first surface 972 and a grasping element second end 996B may be affixed to the apparatus second surface 974. In accordance with the embodiment of FIG. 24, a grasping element second end 1596B may be affixed to a second surface 1574 of apparatus 1556 and a grasping element first end 1596A may be affixed between the first and second apparatus surfaces 1572, 1574. In an embodiment not illustrated, a grasping element first end may be affixed to a second surface of the apparatus and a grasping element second end may be affixed between the first and second apparatus surfaces.

Figure 12:
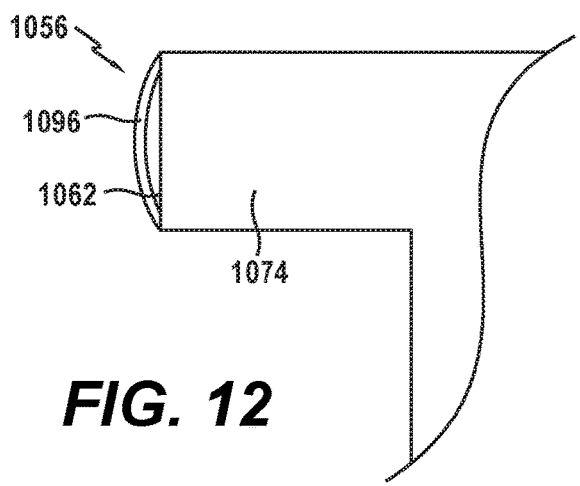
FIG. 12 is plan views of an alternative embodiment of a grasping element for an absorbent article application mat.
Figure 22:
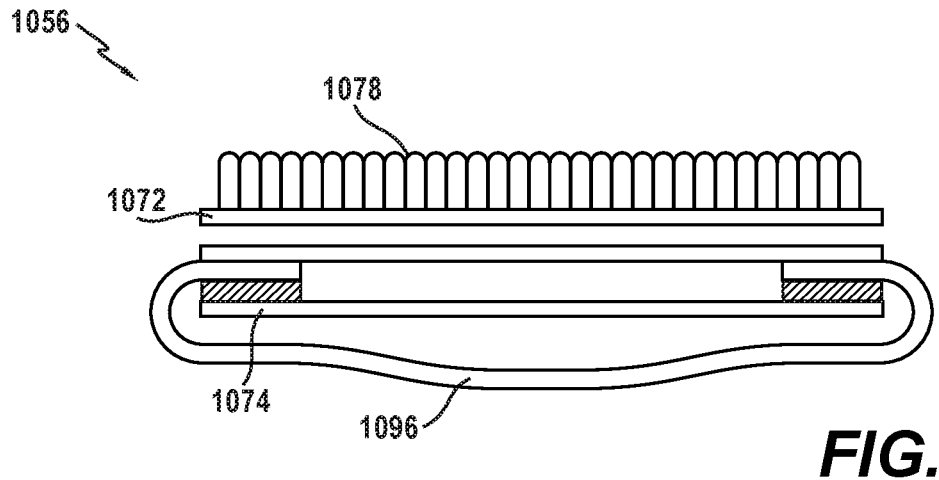
FIG. 22 is a partially exploded side view of an alternative embodiment of absorbent article application mat, including an attachment zone and grasping element.

In accordance with the embodiment of FIGS. 12 and 22, grasping element 1096 first and second ends are respectively attached to each of a top corner and a bottom corner of a lateral element distal end 1062. To attach the grasping element 1096, the grasping element 1096 first and second ends are sandwiched between the apparatus first and second surfaces 1072, 1074. In an embodiment, grasping element first and second ends are applied to a top corner and a bottom corner lateral element distal end of at least one of a first surface and a second surface.

Figure 6:
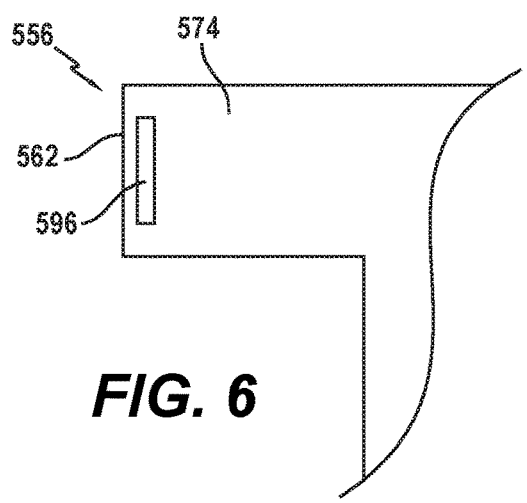
FIG. 6 is plan views of an alternative embodiment of a grasping element for an absorbent article application mat.

In accordance with the embodiment of FIG. 6, grasping elements 596 may be integral to the apparatus 556. That is, the grasping element 596 may be a void formed along and through distal edge portions 560, 562 of the lateral ends of apparatus 556 first and second surfaces 572, 574. The void may be sized to receive at least one of a human finger, fingers and hand. In an alternative embodiment, the void may pass through only one of a first and second surface 572, 574, forming a pocket (not illustrated) along distal edge portions 560, 562 for receiving at least one of a human finger, fingers and hand.

While the embodiments of FIGS. 5-12 illustrate partial views of various embodiments of laterally extending elements and associated grasping elements, it is to be understood that the unillustrated opposite end of the various laterally extending elements and associated grasping elements are mirror images of the illustrated portions.

In accordance with the embodiments of FIGS. 17-24, landing zones 78, 478,678, 778, 878, 1078, 978, 1578 are depicted as extending substantially between a lateral element upper edge portion and lateral element lower edge portion. In alternative embodiments, the landing zone may comprise two or more landings zones positioned in space relation within a perimeter of a lateral element distal end. In another embodiment, a single landing zone may be centrally positioned within a laterally extending element.

In addition to illustrating non-limiting apparatus form factors, FIGS. 25-31 also illustrate non-limiting examples for placement of landing zones and grasping elements. It should be understood that the apparatus form factor, landing zone and grasping element combinations illustrated are for exemplary purposes. The inventor contemplates that any of the disclosed apparatus form factors can be used in combination with any of the landing zones described herein. Similarly, any of the disclosed apparatus form factors can be used in combination with any of the grasping elements described herein.

In the exemplary embodiment of FIG. 25, apparatus 1656 first surface 1672 receives landing zones 1678 placed in space relation to lateral element 1658 distal edge portions 1660, 1662 and second surface 1674 receives grasping elements 1696 placed in space relation to lateral element 1658 distal edge portions 1660, 1662.

Figure 26:
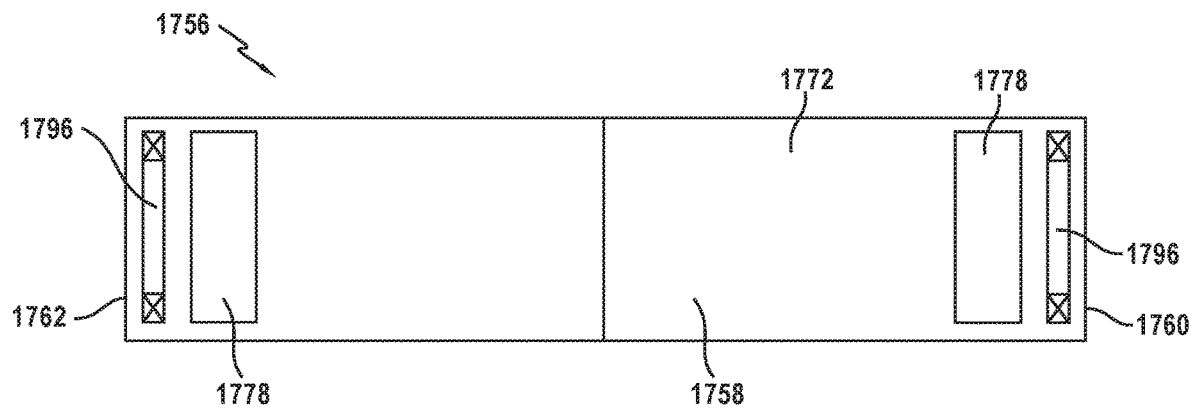
FIG. 26 is a plan view of an alternative embodiment of an absorbent article application mat.
Figure 27:
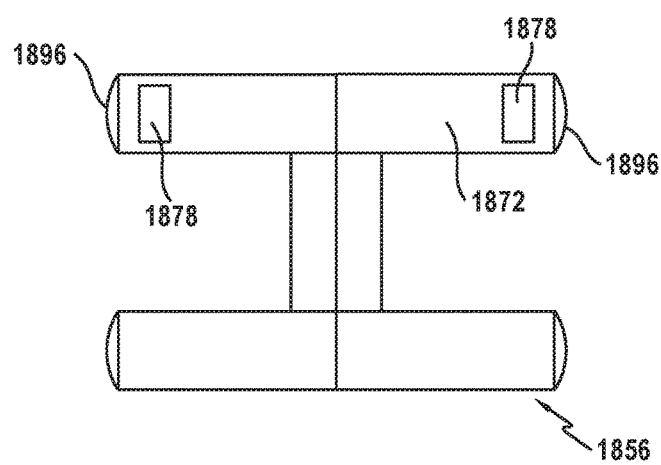
FIG. 27 is a plan view of an alternative embodiment of an absorbent article application mat.

In the exemplary embodiment of FIG. 26, apparatus 1756 first surface 1772 receives landing zones 1778 and grasping elements 1796 placed in space relation to lateral element 1758 distal edge portions 1760, 1762.

In the exemplary embodiment of FIG. 27, apparatus 1856 first surface 1872 receives landing zones 1878 placed in space relation to lateral element 1858 distal edge portions 1860, 1862 and grasping elements 1896 placed at a top corner and a bottom corner of lateral element 1658 distal edge portions 1660, 1662.

Figure 28:
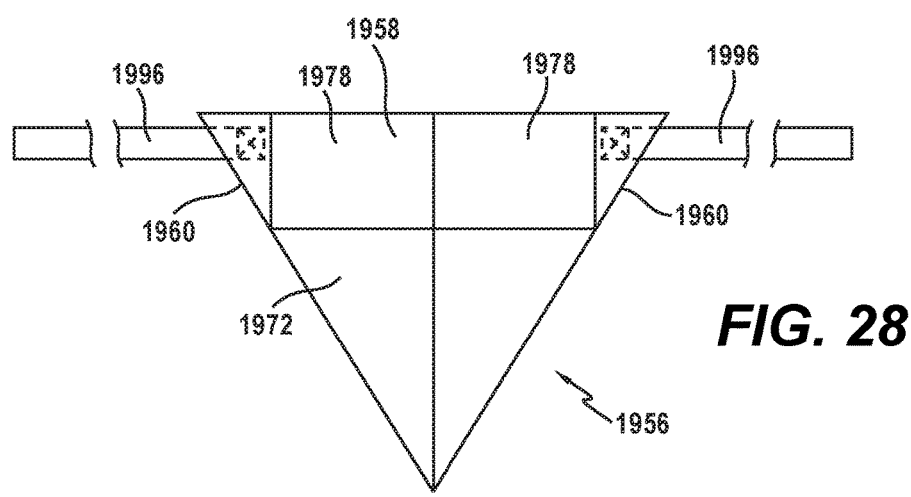
FIG. 28 is a plan view of an alternative embodiment of an absorbent article application mat.

In the exemplary embodiment of FIG. 28, apparatus 1956 first surface 1972 receives landing zones 1978 which extend substantially over a perimeter of laterally extending element and grasping elements 1996 placed in spaced relation to lateral element 1958 distal edge portions 1960, 1962.

Figure 29:
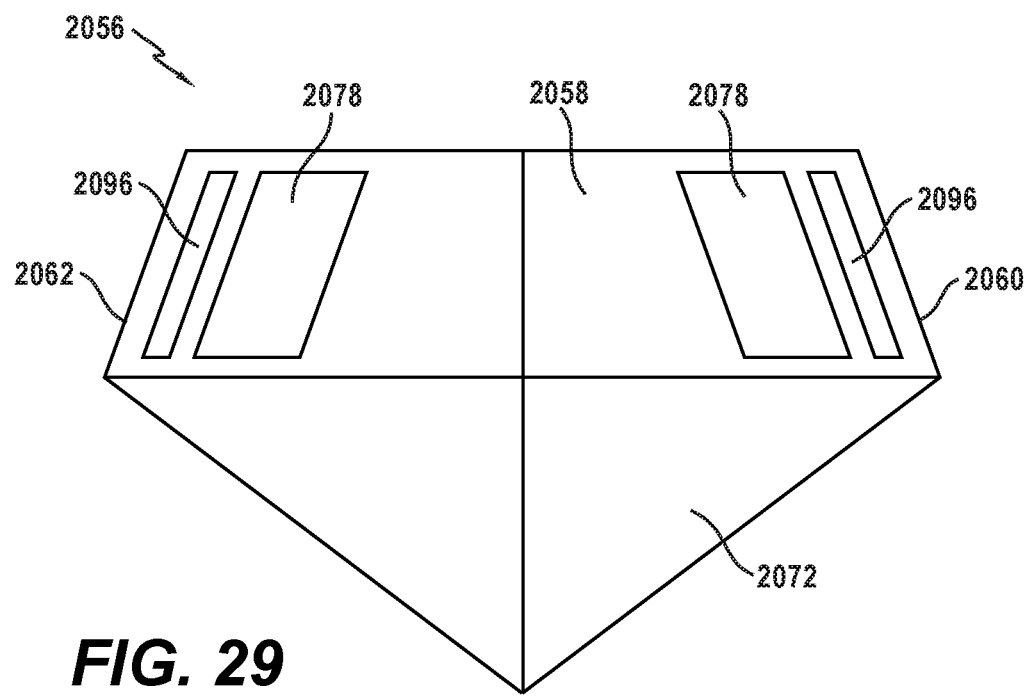
FIG. 29 is a plan view of an alternative embodiment of an absorbent article application mat.
Figure 30:
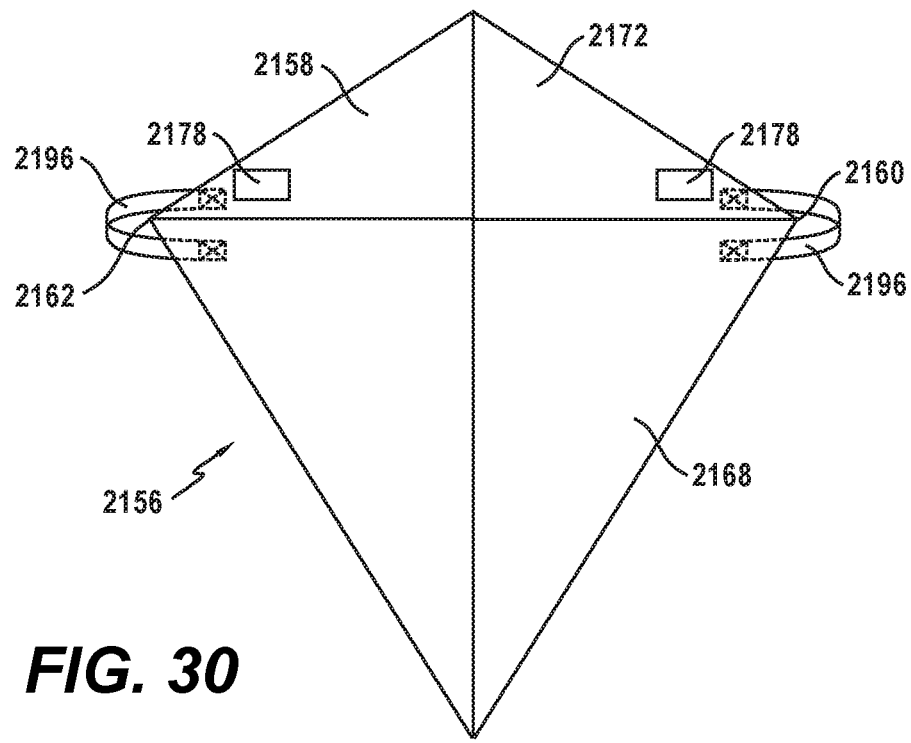
FIG. 30 is a plan view of an alternative embodiment of an absorbent article application mat.

In the exemplary embodiment of FIG. 29, apparatus 2056 first surface 2072 receives landing zones 2078 placed in spaced relation to lateral element 2058 distal edge portions 2060, 2062. In this exemplary embodiment, grasping elements 2096 are voids positioned in in spaced relation to lateral element 2058 distal edge portions 2060, 2062, the voids passing through both lateral element 2058 first and second surfaces 2072, 2074. Alternatively, as discussed above, the voids may pass though only first surface 2072, forming a pocket along distal edge portions 2060, 2062.

In the exemplary embodiment of FIG. 30, apparatus 2156 first surface 2172 receives landing zones 2178 placed in spaced relation to lateral element 2158 distal edge portions 2160, 2162 and grasping elements 2196 placed in spaced relation to lateral element first and second distal edge portions 2160, 2162 on first and second surfaces 2172, 2174 of apparatus 2156. As illustrated, grasping elements 2196 may be placed on both the laterally extending element 2158 and longitudinally extending element 2168.

Figure 31:
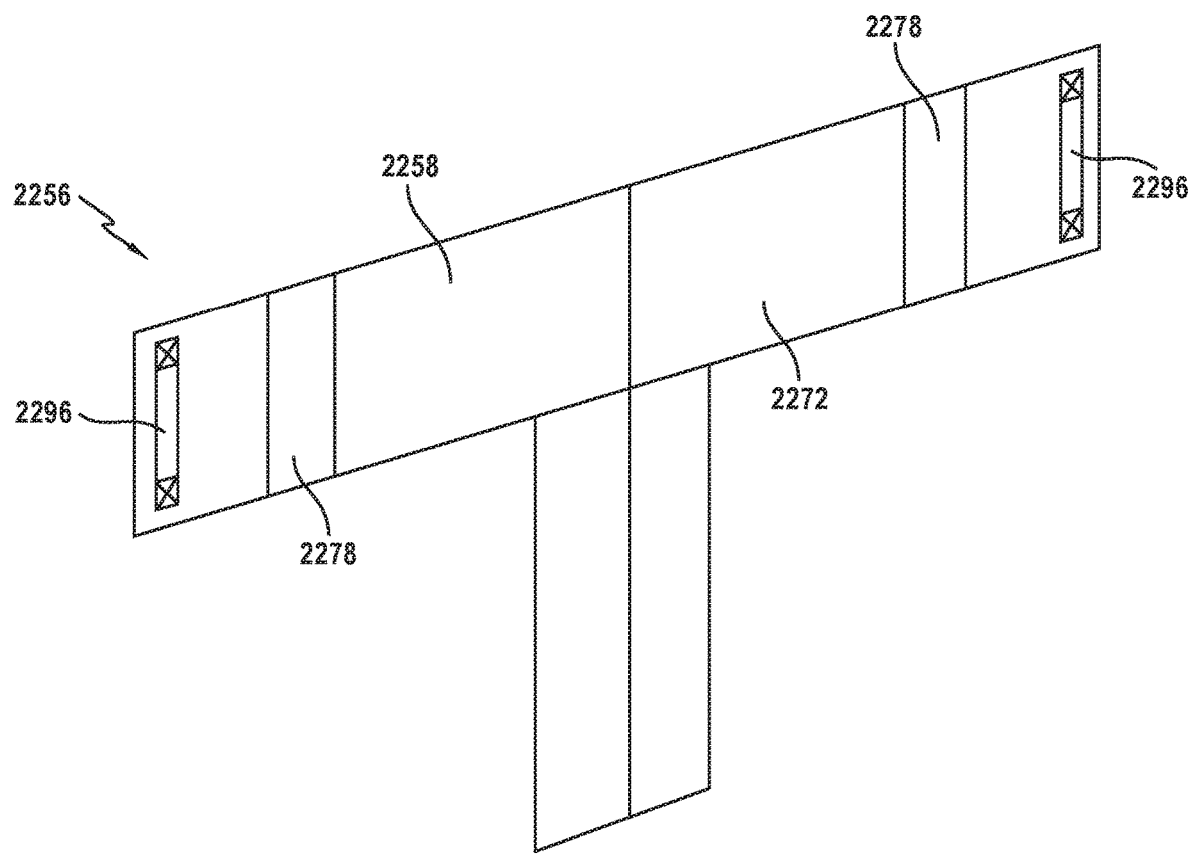
FIG. 31 is a further embodiment of an absorbent article application mat with the attachment zone and grasping element arranged on the same surface.

In the exemplary embodiment of FIG. 31, apparatus 2256 first surface 2272 laterally extending element 2258 receives both the landing zone 2278 and the grasping element 2296.

Returning to FIGS. 1-4, engagement of an absorbent article with the apparatus will be described. While the remainder of the description will be disclosed with respect to FIG. 2A, it should be understood that the embodiments of FIGS. 2B-C may be implemented in a similar manner. To releasably engage an absorbent article 2A with the apparatus 56, a caregiver will extend the absorbent article second portion side panels 18, 20 and fasteners 44 and substantially align the fasteners 44 with the apparatus landing zone 78A, 78B. That is, the first side panel 18 faster 44A-B is joined to a first landing zone 78A and the second side panel 20 fastener 44C-D is joined to a second landing zone 78B. In the embodiments of FIGS. 15 and 16 a first side panel fastener 44A-B is joined to a first distal edge 1360, 1361 of the landing zone 1378, 1379 and a second side panel fastener 44B-C is joined to an opposite distal edge 1362, 1363 of the landing zone 1378, 1379.

Simultaneous to aligning fasteners 44 and landing zones 78, a caregiver is also aligning the absorbent article second portion first and second side panel 18, 20 lower edge portions 40A, 40B along the lower edge portion 66 of the apparatus 56 and visually center the absorbent article 2 along the central axis 70 of the apparatus.

To aid in symmetrical alignment of an absorbent article 2 along the apparatus 56 central axis 70 first surface 72 laterally extending element 58 and the longitudinally extending element 68, a first indicia 100A is included. Non-limiting examples of indicia include a color, a design, a word, a projection, a ridge, a flute, etc. The indicia may be an applied dye, ink, embossing, stitching, welding, etc.

In an embodiment, an absorbent article outer layer 8 may include a complimentary longitudinal central axis indicia. In use, a caregiver will align the apparatus 56 first indicia 100A with the absorbent article indicia to aid in symmetrical alignment of the apparatus and absorbent article.

The apparatus first surface 72 laterally extending element 58 may include a second indicia 100B substantially perpendicular to the first indicia 100A. In an embodiment, the second indicia 100B generally follows the linear extension of the first surface 72 laterally extending element 58 lower edge portion 66 and corresponds with the position from which the longitudinally extending element 68 extends from a lower edge portion 66 of the laterally extending element 58. In an alternative embodiment, the second indicia may be positioned in spaced relation between the first surface laterally extending element upper edge and lower edge portions. In a further alternative embodiment, the second indicia may be positioned along the laterally extending element 58 upper edge portion 64. The characteristics of the second indicia 100B may be the same as or different from the first indicia 100A.

In an embodiment the apparatus second surface 74 may also include first and second indicia 100A', 100B' placed on the apparatus 56 second surface 74 in locations corresponding with the respective placement of the first surface 72 first and second indicia 100A, 100B. The characteristics of second surface 74 first and second indicia 100A', 100B' may be the same as or different from the first and second indicia 100A, 100B. For example, the first surface 72 first indicia 100A may be a ridge and the second surface 74 indicia 100A' may be a line imparted by ink or dye.

In an embodiment at least one of a first and second surface 72, 74 first indicia 100A, 100A' aid a caregiver in aligning an absorbent article 2 central longitudinal axis with a wearer's spine and leg opening and at least one of a first and second surface 72, 74 second indicia 100B, 100B' aid in aligning an absorbent article 2 with a wearer's hip region.

When the combined assembly is placed beneath a wearer, a caregiver, grasping one or more of the grasping elements 96, can align the laterally extending element lower edge 66 portion with a wearer's hip region (at least one of a second indicia 100B, 100B') and align the apparatus 56 central axis 70 with a wearer's spine and leg opening (at least one of a first indicia 100A, 100A') to ensure proper positioning of the absorbent article 2 without tearing or ripping the absorbent article side panels/fasteners 18, 20, 44 during adjustment under a wearer. That is, by coupling an absorbent article 2 with the apparatus 56 and utilizing the grasping elements 96 to position an absorbent article 2 under a wearer, a caregiver is not applying stress to the absorbent article side panels 10, 20 and/or fasteners 44 thereby reducing in incidence of tearing of absorbent article 2 side panels 18, 20 and/or fastener 44 prior to absorbent article application.

Further, as the absorbent article fasteners are attached to the apparatus, the combined assembly provides a caregiver with easier access to the side panels 18, 20. Said differently, side panels 18, 20 are fully extended against the apparatus landing site 80 and are neither folded nor bunched beneath a wearer, therefore aiding in a more symmetrical application of the absorbent article 2 about a wearer's waist, hips and legs.

In an embodiment, once an absorbent article 2 is releasably engaged with the apparatus 56, first surface 72 first and second visual indicia 100A, 100B may longer be visible to a caregiver. Accordingly, in embodiments that do not include second surface 74 first and second indicia 100A', 100B', it is the apparatus form factor which will provide a caregiver with guiding elements for visual alignment of the assembly under a wearer's hip, spine and leg opening.

Following alignment of the assembly with the specific portions of a wearer's body, absorbent article second portion 14 fasteners 44 are disengaged from the apparatus 56 and engaged with the absorbent article first portion 12 complementary fastener. The apparatus 56 can now be removed out from under the wearer.

In an embodiment the apparatus may be single-use disposable or multi-use disposable. In an embodiment the apparatus may be washable, disinfectable and/or capable of being sterilized for reuse.

In the embodiment of FIG. 15 the apparatus 1356 may be sized for use across a range of absorbent article sizes and include one or more size specific landings zones. In an embodiment a landing zone 1378 may include indicia 1378A-C designating fastener placement for a specific absorbent article size. For example, as illustrated in FIG. 15, a landing site 1380 may include the landing zones 1378 for coupling with small, medium and large sized absorbent articles and include corresponding letter indicia.

In an embodiment the apparatus may be sized for use with a specific absorbent article size.

While the present invention has been described with reference to one or more particular embodiments, those skilled in the art will recognize that many changes may be made thereto without departing from the spirit and scope of the present invention. Furthermore, components from one embodiment can be used in other non-exclusive embodiments. Each of these embodiments and obvious various thereof is contemplated as falling within the spirit and scope of the invention, which is set forth in the following alternative embodiments.

What is claimed is:

1. An apparatus for aiding a caregiver in absorbent article application, the apparatus comprising:
    a T-shaped application mat, the mat comprising:
        a substantially flat first surface;
        a substantially flat second surface;
        a laterally extending element, the laterally extending element comprising first and second distal end portions and first upper and lower edge portions, the laterally extending element further comprising a first central longitudinal axis extending between the first upper and lower edge portions;
        a longitudinally extending element comprising second upper and lower edge portions and extending from and substantially perpendicular to the laterally extending element first lower edge portion, the longitudinally extending element further comprising a second central longitudinal axis extending between the second upper and lower edge portions;
    a landing zone;
    a plurality of grasping elements; and
    an indica;
    wherein the first central longitudinal axis and the second central longitudinal axis are substantially aligned;
    wherein the apparatus is adapted to releasably engage an absorbent article for placement of the absorbent article on a wearer; and
    wherein the apparatus is adapted to be disengaged and removed from the absorbent article while the absorbent article remains on the wearer.

2. The apparatus of claim 1, wherein a laterally extending element width is sized to receive at least an overall width of the absorbent article.

3. The apparatus of claim 1, wherein a laterally extending element length is sized to receive at least an overall width of a side panel of the absorbent article.

4. The apparatus of claim 1, wherein the landing zone releasably engages with the absorbent article.

5. The apparatus of claim 1, wherein the landing zone is a plurality of landing zones.

6. The apparatus of claim 1, wherein the landing zone extends over at least a portion of the laterally extending element.

7. The apparatus of claim 1, wherein the indicia is positioned on at least one of the first surface and the second surface.

8. The apparatus of claim 1, wherein the indicia comprises a first, second and third indicia.

9. The apparatus of claim 8, wherein the first indicia extends along the first and second central longitudinal axis.

10. The apparatus of claim 9, whereby the first indicia provides a cue for placement of a central longitudinal axis of the absorbent article.

11. The apparatus of claim 10, whereby the first indicia provides a cue for placement of the absorbent article in relation to a wearer's spine and leg opening.

12. The apparatus of claim 8, wherein the second indicia extends along the laterally extending element lower edge portion.

13. The apparatus of claim 12, whereby the second indicia provides a cue for placement of a side panel lower edge portion of the absorbent article.

14. The absorbent article of claim 13, whereby the second indicia provides a cue for placement of the absorbent article in relation to a wearer's hips.

15. The apparatus of claim 8, whereby the third indicia and the landing zone cooperate based upon a size of the absorbent article.

16. The apparatus of claim 15, whereby the third indicia provides a cue for placement of a range of absorbent article sizes and corresponding fasteners on the landing zone.

17. The apparatus of claim 1, wherein the first surface comprises a low friction material.

18. The apparatus of claim 1, wherein the second surface comprises a material having soft touch properties.

19. The apparatus of claim 1, wherein the apparatus maintains a substantially flat condition when releasably engaging the absorbent article.

20. The apparatus of claim 1, further comprising at least one interfacing layer positioned between the first surface and the second surface.

* * * * *